(12) United States Patent
Fields et al.

(10) Patent No.: US 9,275,552 B1
(45) Date of Patent: *Mar. 1, 2016

(54) REAL-TIME DRIVER OBSERVATION AND SCORING FOR DRIVER'S EDUCATION

(71) Applicant: STATE FARM MUTUAL AUTOMOBILE INSURANCE COMPANY, Bloomington, IL (US)

(72) Inventors: Brian Mark Fields, Normal, IL (US); Jibo He, Champaign, IL (US); John A. Nepomuceno, Bloomington, IL (US); Steve Roberson, Normal, IL (US); Bryan Allen Plummer, Urbana, IL (US); Kurtis C. Houdek, Gurnee, IL (US); Neeraj Jain, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/511,712

(22) Filed: Oct. 10, 2014

Related U.S. Application Data

(63) Continuation of application No. 13/844,090, filed on Mar. 15, 2013, now Pat. No. 8,876,535.

(51) Int. Cl.
  *G09B 9/52* (2006.01)
  *G09B 9/052* (2006.01)
  *G09B 19/14* (2006.01)

(52) U.S. Cl.
  CPC .............. *G09B 9/052* (2013.01); *G09B 19/14* (2013.01)

(58) Field of Classification Search
  CPC combination set(s) only.
  See application file for complete search history.

(56) References Cited

U.S. PATENT DOCUMENTS

| | | | | |
|---|---|---|---|---|
| 5,368,484 A | * | 11/1994 | Copperman et al. | 434/69 |
| 5,499,182 A | * | 3/1996 | Ousborne | 701/29.6 |
| 5,515,026 A | * | 5/1996 | Ewert | 340/436 |
| 5,626,362 A | * | 5/1997 | Mottola | 280/767 |
| 5,835,008 A | * | 11/1998 | Colemere, Jr. | 340/439 |
| 6,253,129 B1 | * | 6/2001 | Jenkins et al. | 701/32.3 |
| 6,313,749 B1 | | 11/2001 | Horne et al. | |
| 6,473,000 B1 | * | 10/2002 | Secreet et al. | 340/936 |
| 6,477,117 B1 | | 11/2002 | Narayanaswami et al. | |
| 6,556,905 B1 | * | 4/2003 | Mittelsteadt et al. | 701/32.4 |
| 6,661,345 B1 | | 12/2003 | Bevan et al. | |
| 6,704,434 B1 | * | 3/2004 | Sakoh et al. | 382/104 |

(Continued)

OTHER PUBLICATIONS

Office Action in U.S. Appl. No. 13/844,090 dated Dec. 4, 2013.

(Continued)

*Primary Examiner* — Robert J Utama
(74) *Attorney, Agent, or Firm* — Marshall, Gerstein & Borun LLP; Randall G. Rueth

(57) ABSTRACT

A method includes, for each of two or more driving sessions in which a student driver operates a vehicle, gathering driving skill data indicative of at least one of behavior of the student driver, acceleration of the vehicle, braking of the vehicle, or steering of the vehicle, and generating a driving session report. The method further includes causing the driving session reports corresponding to the two or more driving sessions to be displayed to a driving instructor, and receiving comments from the driving instructor about the two or more driving sessions of the student driver. Still further, the method includes storing the driving session reports corresponding to the two or more driving sessions along with the received comments from the driving instructor.

20 Claims, 11 Drawing Sheets

(56) References Cited

U.S. PATENT DOCUMENTS

| | | | |
|---|---|---|---|
| 6,909,947 B2* | 6/2005 | Douros et al. | 701/34.4 |
| 7,027,621 B1 | 4/2006 | Prokoski | |
| 7,054,723 B2 | 5/2006 | Seto et al. | |
| 7,138,922 B2 | 11/2006 | Strumolo et al. | |
| 7,149,533 B2 | 12/2006 | Laird et al. | |
| 7,356,392 B2* | 4/2008 | Hubbard et al. | 701/31.5 |
| 7,424,414 B2* | 9/2008 | Craft | 703/8 |
| 7,692,552 B2* | 4/2010 | Harrington et al. | 340/576 |
| 7,719,431 B2 | 5/2010 | Bolourchi | |
| 7,835,834 B2 | 11/2010 | Smith et al. | |
| 8,009,051 B2* | 8/2011 | Omi | 340/575 |
| 8,010,283 B2* | 8/2011 | Yoshida et al. | 701/519 |
| 8,016,595 B2* | 9/2011 | Aoki et al. | 434/61 |
| 8,185,380 B2* | 5/2012 | Kameyama | 704/10 |
| 8,554,468 B1* | 10/2013 | Bullock | 701/408 |
| 8,595,034 B2* | 11/2013 | Bauer et al. | 705/4 |
| 8,876,535 B2 | 11/2014 | Fields et al. | |
| 2002/0146667 A1* | 10/2002 | Dowdell et al. | 434/62 |
| 2004/0005927 A1* | 1/2004 | Bonilla et al. | 463/42 |
| 2004/0017106 A1 | 1/2004 | Aizawa et al. | |
| 2004/0054452 A1* | 3/2004 | Bjorkman | 701/29 |
| 2004/0077285 A1* | 4/2004 | Bonilla et al. | 446/491 |
| 2004/0090334 A1* | 5/2004 | Zhang et al. | 340/575 |
| 2004/0158476 A1* | 8/2004 | Blessinger et al. | 705/1 |
| 2005/0108910 A1* | 5/2005 | Esparza et al. | 40/600 |
| 2005/0131597 A1* | 6/2005 | Raz et al. | 701/29 |
| 2006/0052909 A1* | 3/2006 | Cherouny | 701/1 |
| 2006/0232430 A1 | 10/2006 | Takaoka et al. | |
| 2007/0001831 A1* | 1/2007 | Raz et al. | 340/439 |
| 2007/0080816 A1 | 4/2007 | Haque et al. | |
| 2007/0122771 A1* | 5/2007 | Maeda et al. | 434/62 |
| 2007/0159344 A1 | 7/2007 | Kisacanin | |
| 2008/0064014 A1* | 3/2008 | Wojtczak et al. | 434/69 |
| 2008/0082372 A1* | 4/2008 | Burch | 705/4 |
| 2008/0291008 A1* | 11/2008 | Jeon | 340/539.1 |
| 2010/0055649 A1* | 3/2010 | Takahashi et al. | 434/66 |
| 2010/0131304 A1 | 5/2010 | Collopy et al. | |
| 2010/0214087 A1 | 8/2010 | Nakagoshi et al. | |
| 2011/0090075 A1* | 4/2011 | Armitage et al. | 340/439 |
| 2011/0106370 A1* | 5/2011 | Duddle et al. | 701/33 |
| 2011/0304465 A1 | 12/2011 | Boult et al. | |
| 2011/0307188 A1* | 12/2011 | Peng et al. | 702/33 |
| 2012/0135382 A1* | 5/2012 | Winston et al. | 434/65 |
| 2012/0191343 A1* | 7/2012 | Haleem | 701/431 |
| 2012/0215375 A1* | 8/2012 | Chang | 701/1 |
| 2012/0316406 A1 | 12/2012 | Rahman et al. | |
| 2013/0006674 A1 | 1/2013 | Bowne et al. | |
| 2013/0006675 A1* | 1/2013 | Bowne et al. | 705/4 |
| 2013/0038437 A1 | 2/2013 | Talati et al. | |
| 2013/0073115 A1 | 3/2013 | Levin et al. | |
| 2013/0144459 A1* | 6/2013 | Ricci | 701/1 |
| 2013/0164715 A1* | 6/2013 | Hunt et al. | 434/65 |
| 2013/0189649 A1* | 7/2013 | Mannino | 434/65 |
| 2013/0209968 A1* | 8/2013 | Miller et al. | 434/65 |
| 2014/0047347 A1* | 2/2014 | Mohn et al. | 715/738 |
| 2014/0059066 A1 | 2/2014 | Koloskov | |
| 2014/0099607 A1* | 4/2014 | Armitage et al. | 434/66 |
| 2014/0108198 A1* | 4/2014 | Jariyasunant et al. | 705/26.35 |
| 2014/0167967 A1 | 6/2014 | He et al. | |
| 2014/0168399 A1 | 6/2014 | Plummer et al. | |
| 2014/0172467 A1* | 6/2014 | He et al. | 705/4 |
| 2014/0218187 A1 | 8/2014 | Chun et al. | |
| 2014/0240132 A1 | 8/2014 | Bychkov | |

OTHER PUBLICATIONS

Office Action in U.S. Appl. No. 14/269,490 dated Sep. 12, 2014.
Office Action in U.S. Appl. No. 14/201,491 dated Sep. 26, 2014.
Office Action in U.S. Appl. No. 14/255,934 dated Jun. 18, 2014.
Office Action in U.S. Appl. No. 14/255,934 dated Sep. 23, 2014.
Fields et al., U.S. Appl. No. 14/201,491, filed Mar. 7, 2014.
Fields et al., U.S. Appl. No. 14/255,934, filed Apr. 17, 2014.
Office Action in U.S. Appl. No. 14/511,750 dated Dec. 19, 2014.
Riley et al., U.S. Appl. No. 14/269,490, filed May 5, 2014.
Hancock, G.M., P.A. Hancock, and C.M. Janelle, "The Impact of Emotions and Predominant Emotion Regulation Technique on Driving Performance," pp. 5882-5885, 2012.
McCraty, R., B. Barrios-Choplin, M. Atkinson, and D. Tomasino. "The Effects of Different Types of Music on Mood, Tension, and Mental Clarity." Alternative Therapies in Health and Medicine 4.1 (1998): 75-84. NCBI PubMed. Web. Jul. 11, 2013.
Wiesenthal, David L., Dwight A. Hennessy, and Brad Totten, "The Influence of Music on Driver Stress," Journal of Applied Social Psychology 30, 8, pp. 1709-1719, 2000.

* cited by examiner

REAL-TIME DRIVER OBSERVATION AND SCORING FOR DRIVER'S EDUCATION

RELATED APPLICATIONS

This application is a continuation application of U.S. application Ser. No. 13/844,090, filed Mar. 15, 2013, the disclosure of which is hereby incorporated herein by reference in its entirety for all purposes.

TECHNICAL FIELD

The present disclosure generally relates to a system and a method for observing the driving skills of students in a driver's education class in real-time and, more particularly, to a computer system to collect and analyze the real-time data to provide a quantitative score of the skills of each student driver.

BACKGROUND

One of the most important goals of driving instruction is teaching student drivers how to drive confidently and safely. Driving instructors must teach students how to accelerate, brake, and steer. Driving instructors must also teach students how to watch the road ahead while also checking the rear and side mirrors. However, during live driving sessions, it is difficult for a driving instructor to quantify how well a student driver is demonstrating these skills.

SUMMARY

Accordingly, it may be advantageous use a computer device to observe a student driving during a driving session to gather data about the student driver's performance and generate reports based on the gathered data.

In one embodiment, a method includes, for each of two or more driving sessions in which a student driver operates a vehicle, gathering, from one or more sensors in a mobile device, driving skill data indicative of at least one of behavior of the student driver, acceleration of the vehicle, braking of the vehicle, or steering of the vehicle, and generating, by a module specially configuring a computing device, a driving session report corresponding to the respective one of the two or more driving sessions including calculating, for the respective one of the two or more driving sessions, at least one score based on the driving skill data. The method further includes causing, by the module specially configuring the computing device, the driving session reports corresponding to the two or more driving sessions to be displayed to a driving instructor on a display device, and, in response to displaying the driving session reports corresponding to the two or more driving sessions, receiving comments from the driving instructor about the two or more driving sessions of the student driver. Still further, the method includes storing, by the module on a non-transitory computer-readable medium, the driving session reports corresponding to the two or more driving sessions along with the received comments from the driving instructor.

In another embodiment, a system including a user interface, one or more sensors configured to generate driving skill data indicative of at least one of behavior of a student driver, acceleration of a vehicle, braking of the vehicle, or steering of the vehicle, a non-transitory memory storing computer-readable instructions, and one or more processors. The computer-readable instructions specially configure the one or more processors such that, when executed by the one or more processors, the computer-readable instructions cause the one or more processors to, for each of two or more driving sessions in which the student driver operates the vehicle, gather, from the one or more sensors, the driving skill data indicative of the at least one of behavior of the student driver, acceleration of the vehicle, braking of the vehicle, or steering of the vehicle, and generate a driving session report corresponding to the respective one of the two or more driving sessions including calculating, for the respective one of the two or more driving sessions, at least one score based on the driving skill data. Further, the instructions cause the one or more processors to cause the driving session reports corresponding to the two or more driving sessions to be displayed on the user interface, and, in response to displaying the driving session reports corresponding to the two or more driving sessions, receive, via the user interface, comments about the two or more driving sessions of the student driver. Still further, the instructions cause the one or more processors to store the driving session reports corresponding to the two or more driving sessions along with the received comments.

In yet another embodiment, a non-transitory computer-readable medium stores instructions that specially configure one or more processors of a computer system. When executed by the one or more processors, the instructions cause the computer system to, for each of two or more driving sessions in which a student driver operates a vehicle, gather, from one or more sensors, driving skill data indicative of at least one of behavior of the student driver, acceleration of the vehicle, braking of the vehicle, or steering of the vehicle, and generate a driving session report corresponding to the respective one of the two or more driving sessions including calculating, for the respective one of the two or more driving sessions, at least one score based on the driving skill data. The instructions further cause the computer system to cause the driving session reports corresponding to the two or more driving sessions to be displayed to a driving instructor on a display device, and, in response to displaying the driving session reports corresponding to the two or more driving sessions, receive comments from the driving instructor about the two or more driving sessions of the student driver. Still further, the instruction cause the computer system to store the driving session reports corresponding to the two or more driving sessions along with the received comments from the driving instructor.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
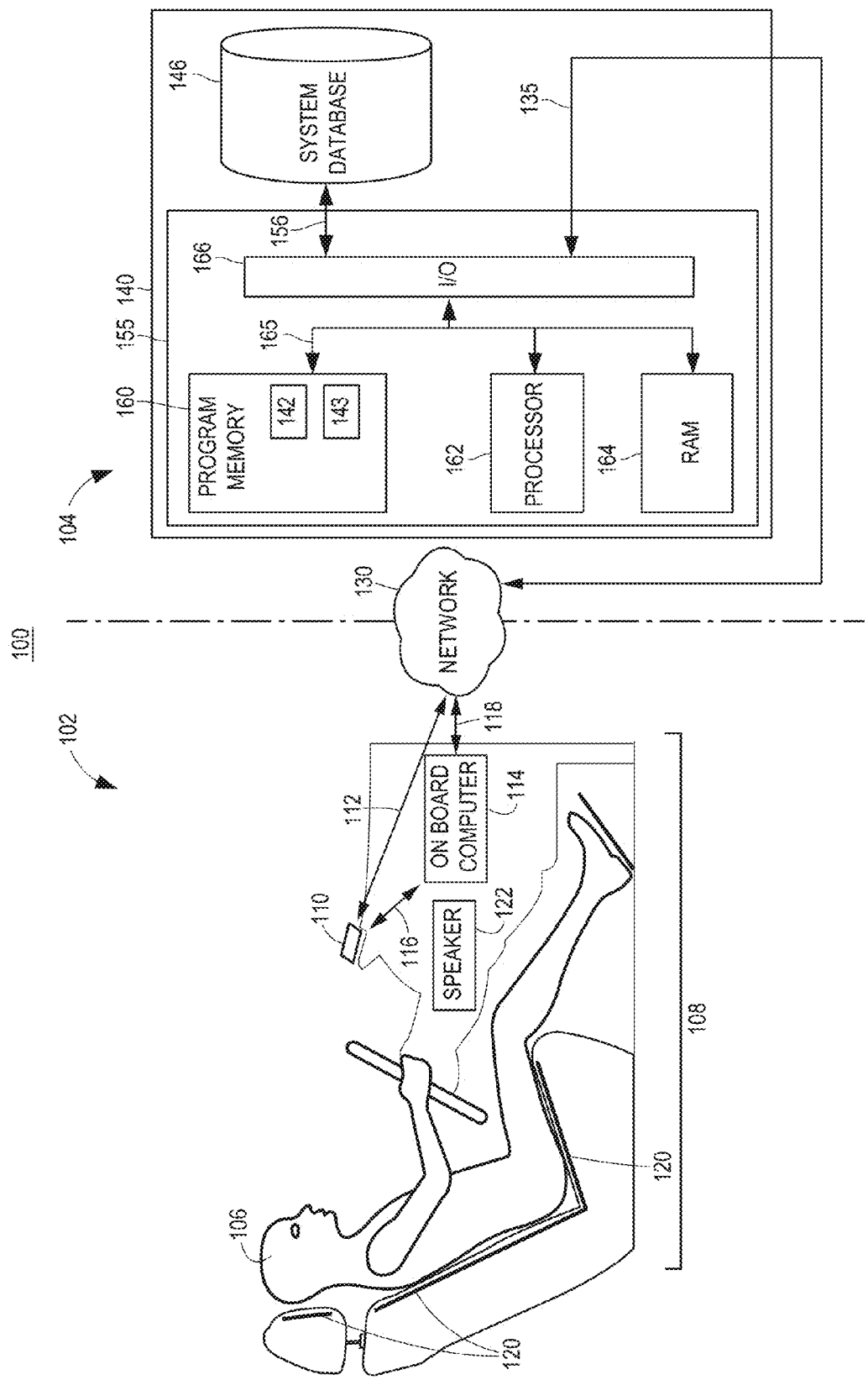
FIG. 1 illustrates a block diagram of a computer network, a computer server, a mobile device, and an on-board computer on which an exemplary driver's education evaluation system and method may operate in accordance with the described embodiments.

FIG. 1 illustrates a block diagram of an exemplary driver's education evaluation system 100. The high-level architecture includes both hardware and software applications, as well as various data communications channels for communicating data between the various hardware and software components. The driver's education evaluation system 100 may be roughly divided into front-end components 102 and back-end components 104. The front-end components 102 are disposed within one or more mobile devices 110. The mobile device 110 may be permanently or removably installed in a vehicle 108 (e.g., a car, truck, etc.). Additionally or alternatively, the vehicle 108 may include an on-board computer 114. The on-board computer 114 may be permanently installed in a vehicle 108 and may interface with various sensors in the vehicle 108 (e.g., a braking sensor, a speedometer, a tachometer, etc.) and/or may interface with various external output devices in the vehicle 108 such as one or more tactile alert systems 120, one or more speakers 122, one or more displays (not shown), etc. The on-board computer 114 may supplement the functions performed by the mobile device 110 described herein by, for example, sending and/or receiving information to and from the mobile device 110. Alternatively, the on-board computer 114 may perform all of the functions of the mobile device 110 described herein. In such cases, no mobile device 110 may be present in the system 100. One or more student drivers 106 may be operating the vehicle 108. The mobile device 110 and on-board computer 114 may communicate with the network 130 over links 112 and 118, respectively. Additionally, the mobile device 110 and on-board computer 114 may communicate with one another directly over link 116. The vehicle 108 may also include a tactile alert system 120 (e.g., a seat that can vibrate) that may present tactile alerts to the vehicle operator 106 on command from the mobile device 110 and/or the on-board computer 114. While shown in a slightly reclined sitting position, those of ordinary skill in the art will appreciate that the student driver 106 could be situated in any number of ways (e.g., reclining at a different angle, standing, etc.) and operating the vehicle using controls other than the steering wheel and pedals shown in FIG. 1 (e.g., one or more sticks, yokes, levers, etc.). The plurality of mobile devices 110 may be located, by way of example rather than limitation, in separate geographic locations from each other, including different areas of the same city, different cities, or different states, and being in mobile vehicles, may move from one geographic location to another.

The front-end components 102 communicate with the back-end components 104 via the network 130. The network 130 may be a proprietary network, a secure public internet, a virtual private network or some other type of network, such as dedicated access lines, plain ordinary telephone lines, satellite links, combinations of these, etc. Where the network 130 comprises the Internet, data communications may take place over the network 130 via an Internet communication protocol. The back-end components 104 include a server 140. The server 140 may include one or more computer processors adapted and configured to execute various software applications and components of the driver's education evaluation system 100, in addition to other software applications. The server 140 further includes a database 146. The database 146 is adapted to store data related to the operation of the driver's education evaluation system 100. Such data might include, for example, data collected by a mobile device 110 and/or on-board computer 114 pertaining to the driver's education evaluation system 100 and uploaded to the server 140 such as images, sensor inputs, data analyzed according to the methods discussed below, or other kinds of data. The server 140 may access data stored in the database 146 when executing various functions and tasks associated with the operation of the driver's education evaluation system 100.

Although the driver's education evaluation system 100 is shown to include one server 140, one mobile device 110, and one on-board computer 114 it should be understood that different numbers of servers 140, devices 110, and on-board computers 114 may be utilized. For example, the system 100 may include a plurality of servers 140 and hundreds of devices 110, all of which may be interconnected via the network 130. As discussed above, the mobile device 110 may perform the various functions described herein in conjunction with the on-board computer 114 or alone (in such cases, the on-board computer 114 need not be present). Likewise, the on-board computer 114 may perform the various functions described herein in conjunction with the mobile device 110 or alone (in such cases, the mobile device 110 need not be present). Furthermore, the processing performed by the one or more servers 140 may be distributed among a plurality of servers 140 in an arrangement known as "cloud computing." According to the disclosed example, this configuration may provide several advantages, such as, for example, enabling near real-time uploads and downloads of information as well as periodic uploads and downloads of information. This may provide for a thin-client embodiment of the mobile device 110 and/or on-board computer 114 discussed herein as well as a primary backup of some or all of the data gathered by the mobile device 110 and/or on-board computer 114. Alternatively, the driver's education evaluation system 100 may include only the front-end components 102. For example, a mobile device 110 and/or on-board computer 114 may perform all of the processing associated with gathering data, generating performance reports for the student driver 106, storing the performance reports, and sending the reports to the back-end components 104 as discussed herein. As such, the driver's education evaluation system 100 may be a "stand-alone" system, neither sending nor receiving information over the network 130.

The server 140 may have a controller 155 that is operatively connected to the database 146 via a link 156. It should be noted that, while not shown, additional databases may be linked to the controller 155 in a known manner. The controller 155 may include a program memory 160, a processor 162 (may be called a microcontroller or a microprocessor), a random-access memory (RAM) 164, and an input/output (I/O) circuit 166, all of which may be interconnected via an address/data bus 165. The program memory 160 may be configured to store computer-readable instructions that when executed by the processor 162 cause the server 140 to implement a server application 142 and a web server 143. The instructions for the server application 142 may cause the server 140 to implement the methods described herein. While shown as a single block in FIG. 1, it will be appreciated that the server application 142 may include a number of different programs, modules, routines, and sub-routines that may collectively cause the server 140 to implement the server application 142. It should be appreciated that although only one microprocessor 162 is shown, the controller 155 may include multiple microprocessors 162. Similarly, the memory of the controller 155 may include multiple RAMs 164 and multiple program memories 160. Further, while the instructions for the server application 142 and web server 143 are shown being stored in the program memory 160, the instructions may additionally or alternatively be stored in the database 146 and/or RAM 164. Although the I/O circuit 166 is shown as a single block, it should be appreciated that the I/O circuit 166 may include a number of different types of I/O circuits. The RAM(s) 164 and program memories 160 may be implemented as semiconductor memories, magnetically readable memories, and/or optically readable memories, for example. The controller 155 may also be operatively connected to the network 130 via a link 135 and the I/O circuit 166.

Figure 2:
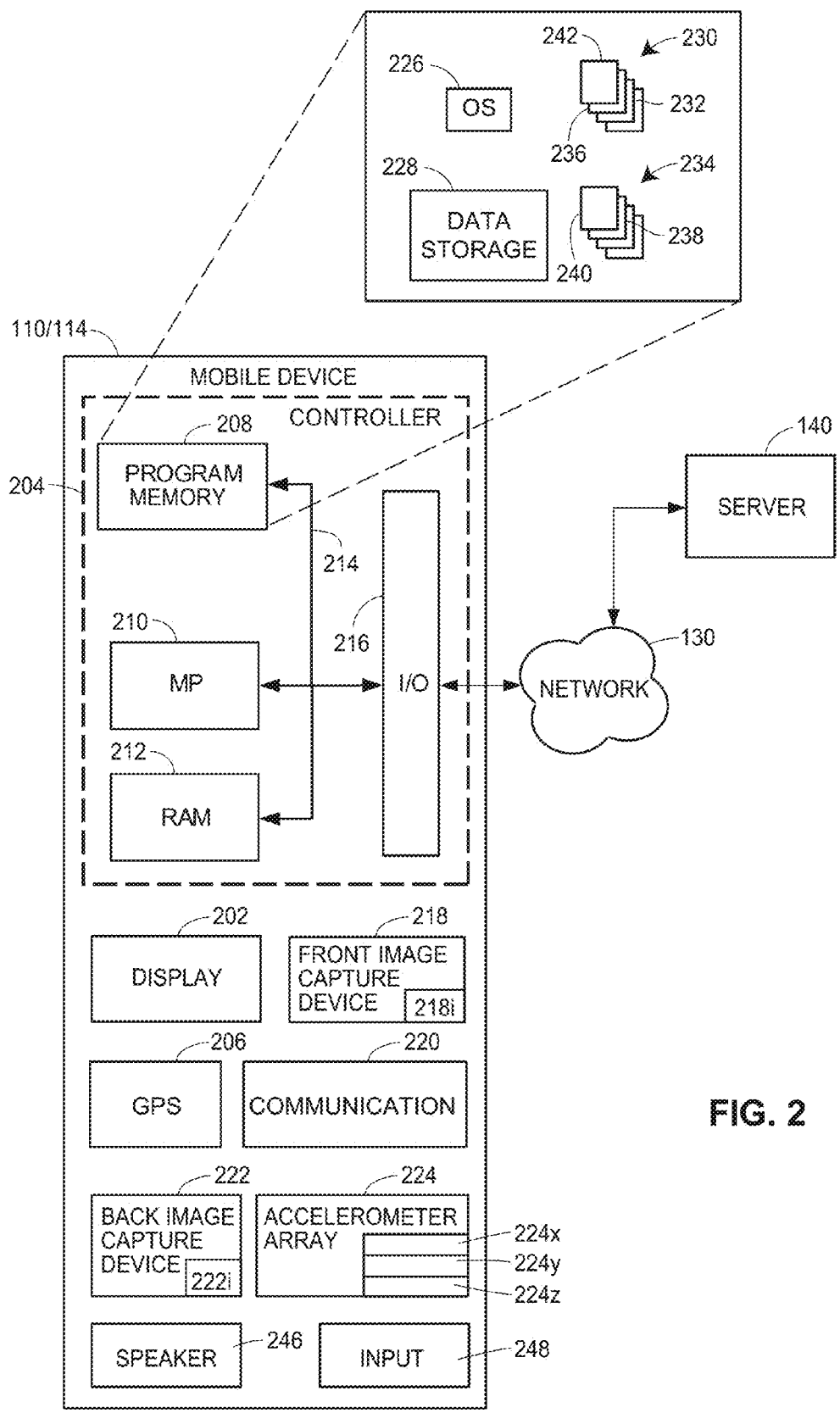
FIG. 2 illustrates a block diagram of an exemplary mobile device.

Referring now to FIG. 2, the mobile device 110 may include a display 202, a Global Positioning System (GPS) unit 206, a communication unit 220, a front image capture device 218, a back image capture device 222, an accelerometer array 224, a user-input device 248, a speaker 246, and, like the server 140, a controller 204. Similarly, the on-board computer 114 may comprise a display 202, a Global Positioning System (GPS) unit 206, a communication unit 220, a front image capture device 218, a back image capture device 222, an accelerometer array 224, a user-input device 248, a speaker 246, and, like the mobile device 110, a controller 204. The mobile device 110 and on-board computer 114 may be integrated into a single device or one can perform the functions of both. It will be appreciated that functions performed by either the mobile device 110 or the on-board computer 114 may also be performed by the on-board computer 114 in concert with the mobile device 110. The mobile device 110 may be either a general-use mobile personal computer, cellular phone, smart phone, tablet computer, other wearable computer (e.g., a watch, glasses, etc.), or a dedicated driver's education evaluation computer. The on-board computer 114 may be a general-use on-board computer capable of performing many functions relating to vehicle operation or a dedicated driver's education evaluation computer. Further, the on-board computer 114 may be installed by the manufacturer of the vehicle 108 or as an aftermarket modification to the vehicle 108. Further, the mobile device 110 and/or on-board computer 114 may be a thin-client device which outsources some or most processing to the server 140.

Similar to the controller 155, the controller 204 includes a program memory 208, one or more microcontroller or a microprocessor (MP) 210, a random-access memory (RAM) 212, and an input/output (I/O) circuit 216, all of which are interconnected via an address/data bus 214. The program memory 208 includes an operating system 226, a data storage 228, a plurality of software applications 230, and a plurality of software routines 234. The operating system 226, for example, may include one of a plurality of mobile platforms such as the iOS®, Android™ Palm® webOS, Windows® Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage 228 may include data such as user profiles and preferences, application data for the plurality of applications 230, routine data for the plurality of routines 234, and other data necessary to interact with the server 140 through the digital network 130. In some embodiments, the controller 204 may also include, or otherwise be communicatively connected to, other data storage mechanisms (e.g., one or more hard disk drives, optical storage drives, solid state storage devices, etc.) that reside within the mobile device 110 and/or on-board computer 114.

The GPS unit 206 may use "Assisted GPS" (A-GPS), satellite GPS, or any other suitable global positioning protocol (e.g., the GLONASS system operated by the Russian government) or system that locates the position the mobile device 110 and/or on-board computer 114. For example, A-GPS utilizes terrestrial cell phone towers or Wi-Fi hotspots (e.g., wireless router points) to more accurately and more quickly determine location of the mobile device 110 and/or on-board computer 114 while satellite GPS generally are more useful in more remote regions that lack cell towers or Wi-Fi hotspots.

The front and back image capture devices 218 and 222 may be built-in cameras within the mobile device 110 and/or on-board computer 114 and/or may be peripheral cameras, such as webcams, cameras installed inside the vehicle 108, cameras installed outside the vehicle 108, etc., that are communicatively coupled with the mobile device 110 and/or on-board computer 114. The front image capture device 218 may be oriented toward the student driver 106 to observe the student driver 106 as described below. The back image capture device 222 may be oriented toward the front of the vehicle 108 to observe the road, lane markings, and/or other objects in front of the vehicle 108. Some embodiments may have both a front image capture device 218 and a back image capture device 222, but other embodiments may have only one or the other. Further, either or both of the front image capture device 218 and back image capture device 222 may include an infrared illuminator 218i, 222i, respectively, to facilitate low light and/or night image capturing. Such an infrared illuminator 218i, 222i may be automatically activated when light is insufficient for image capturing.

The accelerometer array 224 may be one or more accelerometers positioned to determine the force and direction of movements of the mobile device 110 and/or on-board computer 114. In some embodiments, the accelerometer array 224 may include an X-axis accelerometer 224x, a Y-axis accelerometer 224y, and a Z-axis accelerometer 224z to measure the force and direction of movement in each dimension respectively. It will be appreciated by those of ordinary skill in the art that a three dimensional vector describing a movement of the mobile device 110 and/or on-board computer 114 through three dimensional space can be established by combining the outputs of the X-axis, Y-axis, and Z-axis accelerometers 224x, y, z using known methods. The GPS unit 206, the front image capture device 218, the back image capture device 222, and accelerometer array 224 may be referred to collectively as the "sensors" of the mobile device 110 and/or on-board computer 114. Of course, it will be appreciated that additional GPS units 206, front image capture devices 218, back image capture devices 222, and/or accelerometer arrays 224 may be added to the mobile device 110 and/or on-board computer 114.

The communication unit 220 may communicate with the server 140 via any suitable wireless communication protocol network, such as a wireless telephony network (e.g., GSM, CDMA, LTE, etc.), a Wi-Fi network (802.11 standards), a WiMAX network, a Bluetooth network, etc. The communication unit 220 may also be capable of communicating using a near field communication standard (e.g., ISO/IEC 18092, standards provided by the NFC Forum, etc.). Further, the communication unit 220 may use a wired connection to the server 140.

The user-input device 248 may include a "soft" keyboard that is displayed on the display 202 of the mobile device 110 and/or on-board computer 114, an external hardware keyboard communicating via a wired or a wireless connection (e.g., a Bluetooth keyboard), an external mouse, or any other suitable user-input device. The user-input device 248 may also include a microphone capable of receiving user voice input. As discussed with reference to the controllers 155 and 224, it should be appreciated that although FIG. 2 depicts only one microprocessor 210, the controller 204 may include multiple microprocessors 210. Similarly, the memory of the controller 204 may include multiple RAMs 212 and multiple program memories 208. Although the FIG. 2 depicts the I/O circuit 216 as a single block, the I/O circuit 216 may include a number of different types of I/O circuits. The controller 204 may implement the RAM(s) 212 and the program memories 208 as semiconductor memories, magnetically readable memories, and/or optically readable memories, for example.

The one or more processors 210 may be adapted and configured to execute any of one or more of the plurality of software applications 230 and/or any one or more of the plurality of software routines 234 residing in the program memory 208, in addition to other software applications. One of the plurality of applications 230 may be a client application 232 that may be implemented as a series of machine-readable instructions for performing the various tasks associated with implementing the driver's education evaluation system 100 as well as receiving information at, displaying information on, and transmitting information from the mobile device 110 and/or on-board computer 114. The client application 232 may function to implement a stand-alone system or as a system wherein the front-end components 102 communicate with back-end components 104 as described herein. The client application 232 may include machine-readable instruction for implementing a user interface to allow a user to input commands to and receive information from driver's education evaluation system 100. One of the plurality of applications 230 may be a native web browser 236, such as Apple's Safari®, Google Android™ mobile web browser, Microsoft Internet Explorer® for Mobile, Opera Mobile™, that may be implemented as a series of machine-readable instructions for receiving, interpreting, and displaying web page information from the server 140 or other back-end components 104 while also receiving inputs from the user. Another application of the plurality of applications may include an embedded web browser 242 that may be implemented as a series of machine-readable instructions for receiving, interpreting, and displaying web page information from the servers 140 or other back-end components 104 within the client application 232. One of the plurality of routines may include an image capture routine 238 that coordinates with the image capture devices 218, 222 to retrieve image data for use with one or more of the plurality of applications, such as the client application 232, or for use with other routines. Another routine in the plurality of routines may include an accelerometer routine 240 that determines the force and direction of movements of the mobile device 110 and/or on-board computer 114. The accelerometer routine 240 may process data from the accelerometer array 224 to determine a vector describing the motion of the mobile device 110 and/or on-board computer 114 for use with the client application 232. In some embodiments where the accelerometer array 224 has X-axis, Y-axis, and Z-axis accelerometers 224x, y, z, the accelerometer routine 240 may combine the data from each accelerometer 224x, y, z to establish a vector describing the motion of the mobile device 110 and/or on-board computer 114 through three dimensional space. Furthermore, in some embodiments, the accelerometer routine 240 may use data pertaining to less than three axes, such as when determining when the vehicle 108 is braking.

A user may launch the client application 232 from the mobile device 110 and/or on-board computer 114, to access the server 140 to implement the driver's education evaluation system 100. Additionally, the customer or the user may also launch or instantiate any other suitable user interface application (e.g., the native web browser 236, or any other one of the plurality of software applications 230) to access the server 140 to realize the driver's education evaluation system 100.

The server 140 may further include a number of software applications. The various software applications are responsible for generating the data content to be included in the web pages sent from the web server 143 to the mobile device 110 and/or on-board computer 114. The software applications may be executed on the same computer processor as the web server application 143, or on different computer processors.

In embodiments where the mobile device 110 and/or on-board computer 114 is a thin-client device, the server 140 may perform many of the processing functions remotely that would otherwise be performed by the mobile device 110 and/or on-board computer 114. In such embodiments, the mobile device 110 and/or on-board computer 114 may gather data from its sensors as described herein, but instead of analyzing the data locally, the mobile device 110 and/or on-board computer 114 may send the data to the server 140 for remote processing. The server 140 may perform the analysis of the gathered data to evaluate the driving performance of the student driver 106 as described below. If the server 140 determines that the student driver 106 may be impaired, the server 140 may command the mobile device 110 and/or on-board computer 114 to alert the student driver as described below. Additionally, the server 140 may generate the metrics and suggestions described below based on the gathered data.

Figure 3:
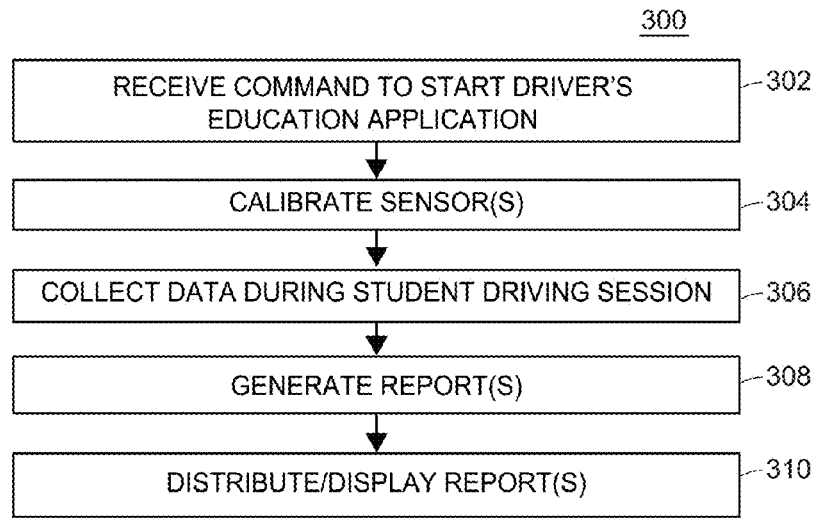
FIG. 3 depicts an exemplary driver's education evaluation monitoring method for implementing the driver's education evaluation system in accordance with the presently described embodiments.

FIG. 3 is a flow diagram depicting an exemplary embodiment of a driver's education evaluation method 300 implemented by the driver's education evaluation system 100. More particularly the method 300 may be performed by the mobile device 110 and/or on-board computer 114 and/or the mobile device 110 and/or on-board computer 114 in conjunction with the server 140. The method 300 may be initiated by a command (block 302). The command may be a user command received by the mobile device 110 and/or on-board computer 114 via the client application 232. Alternatively or additionally, the command may be sent by the server 140 or may be generated automatically by the mobile device 110 and/or on-board computer 114 after the meeting of a condition (e.g., the vehicle 108 has been started; the mobile device 110 is within a specified distance from the vehicle, a certain time, etc.). Next, the sensors of the mobile device 110 and/or on-board computer 114 may be calibrated (block 304). For example the front image capture device 218 may attempt to detect the face and eye(s) of the student driver 106. Calibration may further entail adjusting the front image capture device 218 to account for the student driver's 106 skin tone, facial characteristics, etc., ambient light in the vehicle, the background behind the student driver 106, etc. The back image capture device 222 may also be calibrated, such as, to attempt to detect the road in front of the vehicle, identify lane markings, and identify other vehicles on the road. Calibration may further entail adjusting the back image capture device 222 to account for the color of the road, road conditions (e.g., a wet road from rain or an icy road from snow), the color of lane markings, the time of day and ambient light, etc. The accelerometer array 224 may also be calibrated. Such calibration may include accounting for constant vibration (e.g., the vibration caused by the engine of the vehicle 108) or other repetitive forces applied to the mobile device 110 and/or on-board computer 114.

Figure 4:
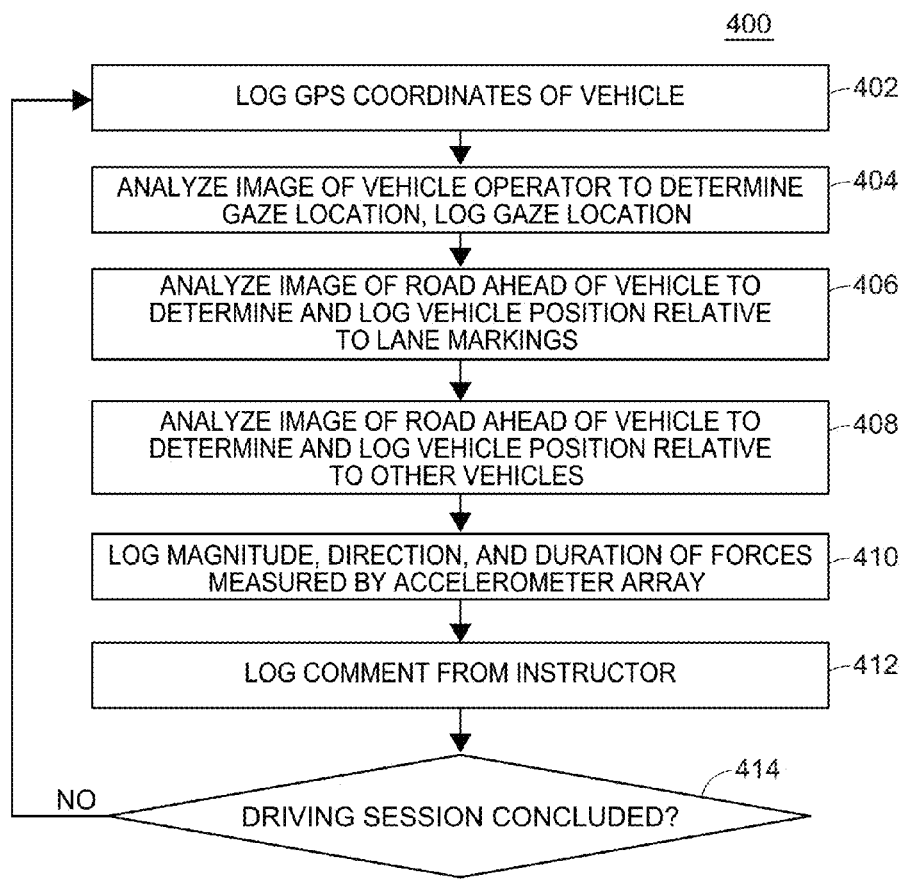
FIG. 4 depicts an exemplary primary indicator logging method for implementing the driver's education evaluation system in accordance with the presently described embodiments.

After calibration, the mobile device 110 and/or on-board computer 114 may begin to collect data about student driver performance using the sensor(s) on the mobile device 110 and/or on-board computer 114 (block 306). FIG. 4 is a flow diagram depicting an exemplary embodiment of a primary performance indicator logging method 400 implemented by the driver's education evaluation system 100 while gathering data about student driver performance at block 306. Performance indicators may be a series of measurements of conditions or characteristics pertaining to student driver performance. Accordingly, the front image capture device 218, back image capture device 222, and accelerometer array 224, may be used to measure these conditions and characteristics. Such measurements may be logged periodically (e.g., every millisecond, every second, etc.) or maybe logged conditionally on the occurrence of an event (e.g., a force of a magnitude above a certain threshold is detected) and stored in data storage 228 as a performance indicator log. Such performance indicator logs may also include a timestamp to note the time of the measurement and/or a location stamp to note the GPS coordinates of the measurement. The driver's education evaluation system 100 may make performance indicator logs for primary performance indicators such as: student driver gaze location, vehicle position relative to lane markings, vehicle position relative to other vehicles; and acceleration along the X, Y, or Z axes. The driver's education evaluation system 100 may derive secondary performance indicators from the primary performance indicators such as: student driver gaze fixation, lane deviation, failure to maintain lane centering, time to collision, time to brake, time to react, longitudinal vehicle control, vehicle braking, vehicle acceleration, and lateral acceleration. Both the primary performance indicator logs and secondary performance indicator logs may be logged separately (e.g., a log for gaze location, a log for X axis force, etc.) or may be logged together. These separate or integrated logs may be stored in data storage 228 or may be transmitted to the server 140 via the network 130 for remote storage.

In order to include a location stamp for each performance log that may be recorded, the mobile device 110 and/or on-board computer 114 may take a reading from the GPS unit 206 to determine current location of the vehicle 108 (block 402). As discussed above, a location stamp may be recorded for each performance log. Accordingly, it may be advantageous to take a reading from the GPS unit 206 prior to recording any performance log. Additionally, with a series of GPS location logs, the velocity of the vehicle 108 may be determined. Further, if speed limit data about the route taken is available, a series of GPS location logs and a calculated velocity may be used to make a determination about whether the student driver 106 is maintaining a speed above a minimum speed limit and/or below a maximum speed limit. Student driver gaze location may be determined by monitoring the eye or eyes of student driver 106 with the front image capture device 218 (block 404). Student driver gaze location may be logged as the horizontal and vertical coordinates of the student drive's apparent gaze. Student driver gaze location may be used to determine when the student driver 106 is looking at the road, mirrors, the dashboard, stereo or air conditioning controls, a mobile device, etc. In some embodiments, the client application 232 may log whether the student driver 106 is looking at a distraction (e.g., the stereo) or in the direction of an important area for vehicle operation (e.g., the road, mirrors, etc.). The driver's education evaluation system 100 may differentiate between the important areas for vehicle operation in gaze location logs. The driver's education evaluation system 100 may include a first value in the gaze location log indicating that the student driver was looking at the road, a second value in the gaze location log indicating that the student driver was looking at the rear view mirror, a third value in the gaze location log indicating that the student driver was looking at the left side mirror, a fourth value in the gaze location log indicating that the student driver was looking at the right side mirror, and a fifth value in the gaze location log indicating that the vehicle was looking at the dashboard gauges (e.g., speedometer). The client application 232 may also include a timestamp and/or location stamp in the gaze location log. If a gaze location log is made every time the student driver starts looking at a different object, then the duration of a particular student driver gaze can be determined by the difference between the time the student driver 106 began looking at the object and the time the student driver 106 begins looking at another object.

The back image capture device 222 may be used to monitor conditions on the road including identifying lane markings and/or other vehicles on the road. Vehicle position relative to lane markings may be determined by processing an image or series of images captured by the back image capture device 222 to determine the distance of the vehicle 108 from lane markings on either or both sides of the vehicle 108 (block 406). The mobile device 110 and/or on-board computer 114 may determine vehicle position relative to lane markings regularly with a timestamp and/or location stamp and store the log of vehicle position relative to lane markings in data storage 228 or send the log of vehicle position relative to lane markings to the server 140 for remote storage. Similarly, vehicle position relative to other vehicles (also referred to as vehicle headway distance) may be determined by processing an image or series of images captured by the back image capture device 222 to determine the distance of the vehicle 108 from other vehicles on the road in front of the vehicle 108 (block 408). For example, the images captured by the back image capture device 222 may be analyzed to compare the visual area of an object in front of the vehicle in one or more images (i.e., if the visual area is larger in a first image relative to a second image, the object was likely closer at the time the second image was captured whereas if the visual area of the object is smaller in a first image relative to a second image, the object was likely further away at the time the second image was captured) and/or the visual area of the road between the vehicle 108 and an object (i.e., if the visual area of the road is larger in a first image relative to a second image, the object was likely further away at the time the second image was captured whereas if the visual area of the road is smaller in a first image relative to a second image, the object was likely closer at the time the second image was captured). Additionally or alternatively, if the back image capture device 222 is properly calibrated, a single image of the road ahead of the vehicle may be sufficient to estimate the distance of the vehicle 108 from the vehicle ahead using known trigonometric principles. The mobile device 110 and/or on-board computer 114 may determine vehicle position relative to other vehicles regularly with a timestamp and store the log in data storage 228 or send the log to the server 140 for remote storage. Additionally, information from the GPS unit 206 may be incorporated into the log to add information about the current velocity and/or location of the vehicle 108.

The accelerometer array 224 may be used to monitor forces on the vehicle in the X, Y, and/or Z axis and create accelerometer logs (block 410). In some embodiments, the Y-axis may be oriented along left to right axis of the mobile device 110 and/or on-board computer 114, the Z-axis may be oriented along the top to bottom axis of the mobile device 110 and/or on-board computer 114, and the X-axis may be oriented along the front to back axis of the mobile device 110 and/or on-board computer 114. However, the axes could be oriented in any number of ways. The mobile device 110 and/or on-board computer 114 may determine the magnitude of a force along one of the axes and make an accelerometer log with a timestamp and/or location stamp in data storage 228 or send the accelerometer log to the server 140 for remote storage.

The user input device 248 may be used to collect comments from the driving instructor during the driving session (block 412). By activating a control (for example the "Create Note" button 1004 of FIG. 10), the driving instructor may create a comment or note about the driving session. The driving instructor may record an audible comment or type a textual comment. For example, the driving instructor may make a comment after instances of poor driving performance such as the student driver 106 stopping in a crosswalk, crossing the center line of the street, applying the brakes too late, etc. The driving instructor may also make comments after instances of good driving performance such as a well executed turn. The comments may be related to a particular action (e.g., a particularly well executed turn) or general comments about the driving session (e.g., "Sam has shown a marked improvement since the session last week."). The instructor may make notes during and/or after the driving session. Comments may be entered by the instructor directly on the first mobile device 110 and/or on-board computer 114 performing the student driver performance evaluation methods discussed herein, or comments may be entered via a second mobile device 110 in communication with the first mobile device 110 and/or on-board computer 114. For example, the driving instructor may use a tablet computer to record comments which are relayed to the first mobile device 110 and/or on-board computer 114 via Bluetooth® or Near Field Communication or any known short-range networking technique. Alternatively, the second mobile device 110 may communicate with the first mobile device 110 and/or on-board computer 114 via the network 130. The comments may be stored with a timestamp and/or location stamp in data storage 228 or sent to the server 140 for remote storage If the student driver session has concluded, the primary performance indicator logging method 400 may end. However if the student driving session has not concluded, the primary performance indicator logging method 400 may continue to gather data (block 414).

Figure 5A:
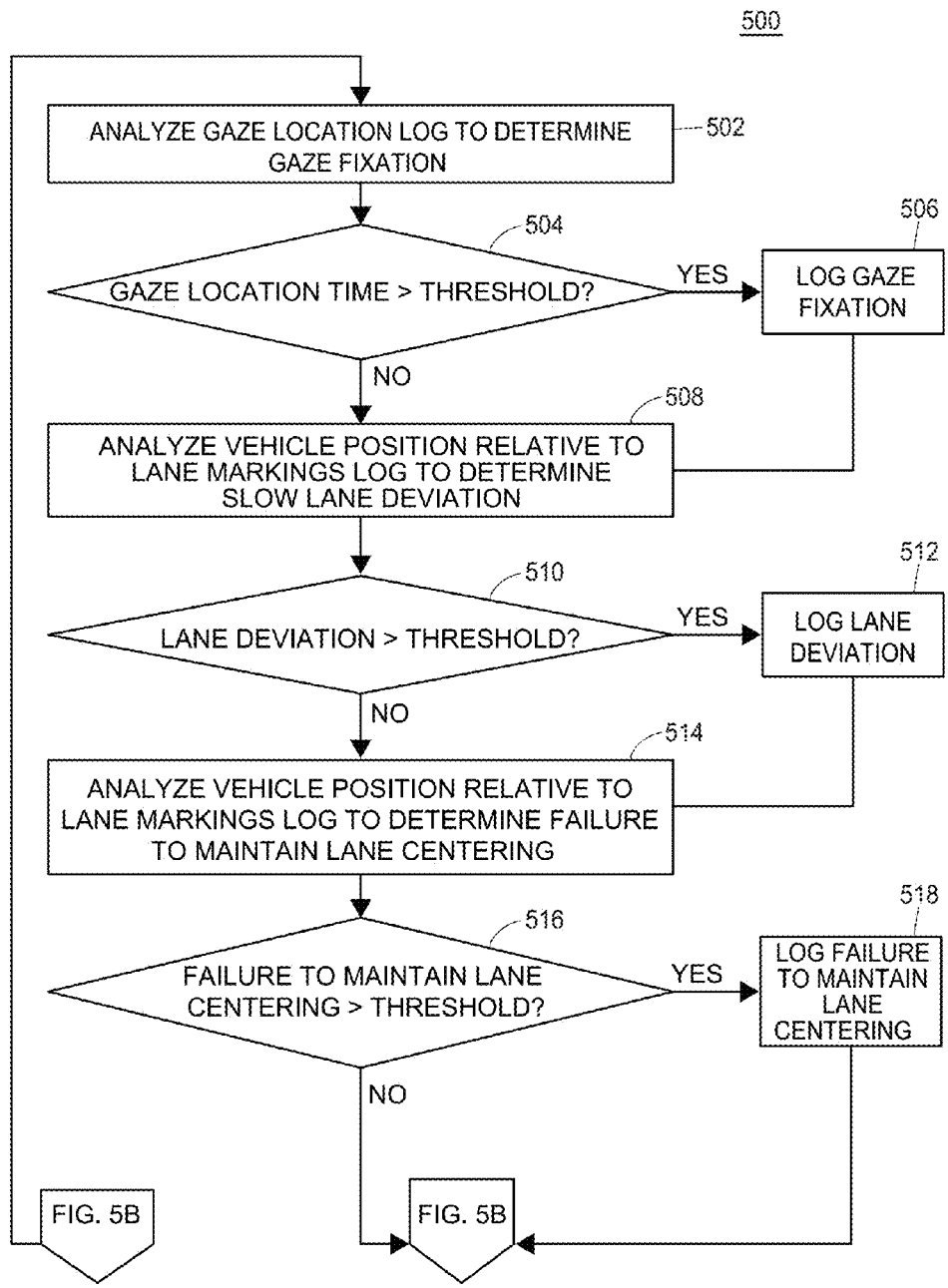
FIGS. 5A-B depict an exemplary secondary performance indicator logging method for implementing the driver's education evaluation system in accordance with the presently described embodiments.
Figure 5B:
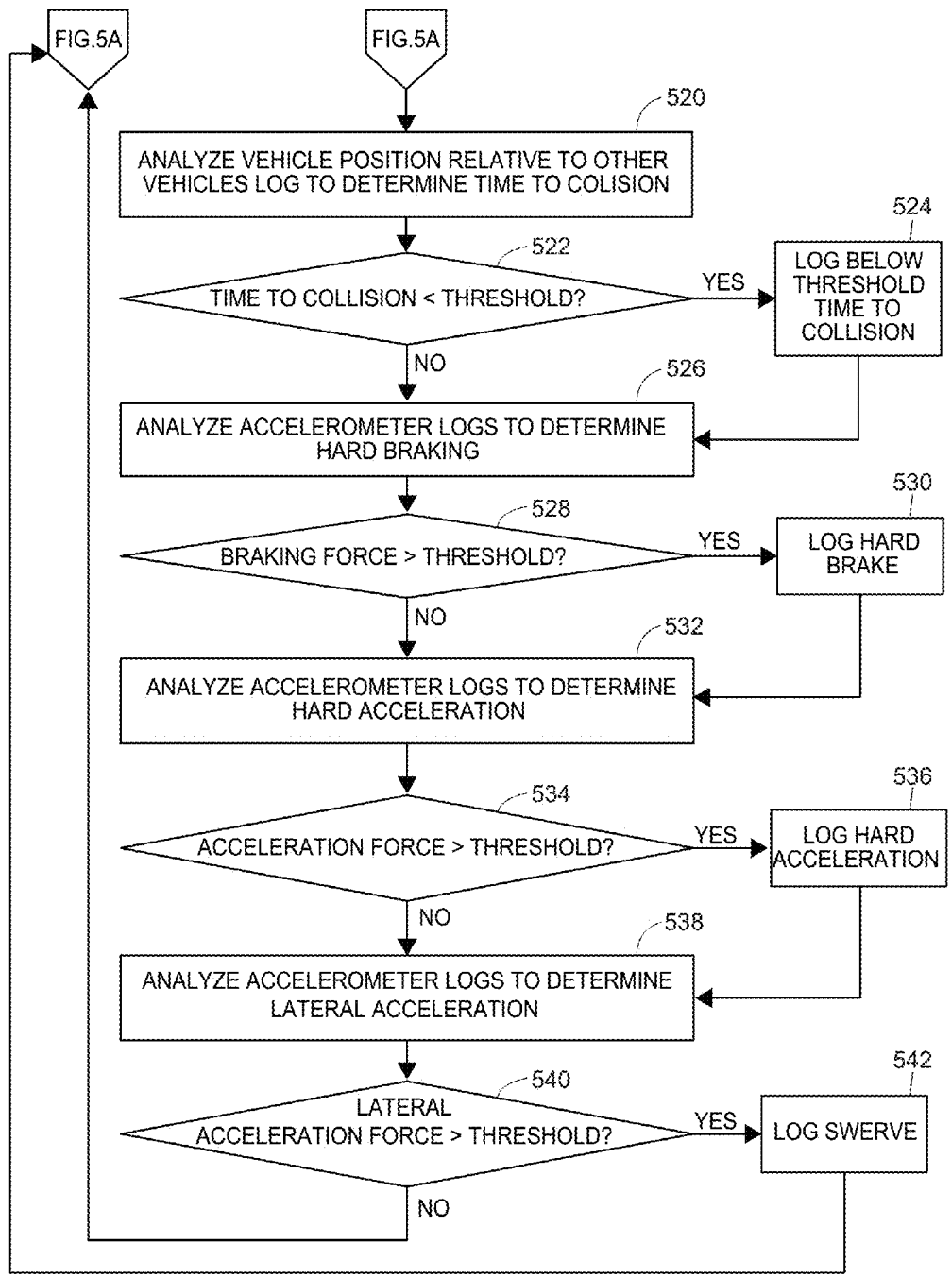

FIGS. 5A-B are flow diagrams depicting an exemplary embodiment of a secondary performance indicator logging method 500 implemented by the driver's education evaluation system 100 while gathering data about potential student driver performance at block 306. Referring to FIG. 5A, student driver gaze fixation may be determined by analyzing a set of student driver gaze location logs and determining the length of time in which the student driver 106 is looking at a particular place (block 502). It will be understood that when looking at a particular place, a student driver 106 may move his or her eyes slightly. Such minor variations may be disregarded subject to a sensitivity setting. Student driver gaze fixation records instances where a student driver has looked at the same object for more than a threshold period of time (e.g., 100 ms) (block 505). For example, student driver gaze fixation may be used to detect when the student driver 106 has his or her gaze fixed on the road above a threshold level (e.g., the student driver 106 has not looked at mirrors or dashboard in more than two seconds). Additionally or alternatively, student driver gaze fixation may be determined by analyzing a set of student driver gaze location logs and determining the eye movement of the student driver 106 by calculating the degree to which the student driver's 106 eyes have moved in a first image relative to a second image. When employing such an eye movement velocity-based gaze detection algorithm, student driver gaze fixation may record instances where the velocity of eye movement is below a threshold value (e.g., thirty-five degrees per second). If student driver gaze fixation is detected, the client application 232 may make a gaze fixation log with a timestamp and/or location stamp (block 506).

With the logs of vehicle position relative to lane markings, lane deviation may be determined by analyzing the logs of vehicle position relative to lane markings to determine when the distance between a lane marking and vehicle 108 indicates that the vehicle 108 has changed lanes (block 508). While lane changes are a normal aspect of vehicle operation, a slow lane change may indicate that the operator 106 is not properly controlling the vehicle 108 and/or is distracted. Accordingly, the driver's education evaluation system 100 may analyze the log of vehicle position relative to lane markings to detect lane changes that occur over a period of time greater than a threshold value (e.g., twenty seconds, thirty seconds, etc.) (block 510). When a slow lane deviation is detected, the client application may make a slow lane deviation log with a timestamp and/or location stamp (block 512).

With the logs of vehicle position relative to lane markings, failure to maintain lane centering may be determined by analyzing the logs of vehicle position relative to lane markings to determine when the distance between a lane marking and vehicle 108 indicates that the vehicle 108 is not centered in the lane (block 514). Similarly to lane deviation, if a vehicle 108 starts to veer from the center of the lane over a long period of time, this may indicate that the student driver 106 is not properly controlling the vehicle 108 and/or is distracted. Accordingly, the driver's education evaluation system 100 may analyze the log of vehicle position relative to lane markings to detect an increasing failure to maintain lane centering that occurs over a period of time greater than a threshold value (e.g., fifteen seconds) (block 516). When a failure to maintain lane centering is detected, the client application 232 may make a log with a timestamp and/or location stamp (block 518).

Referring now to FIG. 5B, with the logs of vehicle position relative to other vehicles, time to collision may be determined by analyzing the logs of vehicle position relative to other vehicles to determine when a decreasing time to collision indicates that the vehicle 108 may be too close behind another vehicle (block 520). Time to collision may be calculated in a number of ways (e.g., by dividing the distance between the vehicle 108 and the vehicle ahead by the difference in velocity between the two vehicles, etc.). Next, the client application 232 may determine the visual area of an object in front of the vehicle 108 in a first image, determine the visual area of the object in a second image, and calculate the difference between the two areas. Then, the time to collision may be estimated by noting the change in the difference between the two areas relative to the amount of time between the first time and the second time. Additionally or alternatively, the client application 232 may determine the visual area of the road in front of the vehicle 108 in a first image, determine the visual area of the road in a second image, and calculate the difference between the two areas. Then, the time to collision may be estimated by noting the change in the difference between the two areas relative to the amount of time between the first time and the second time. Alternatively, the distance between the vehicle 108 and the vehicle ahead may be calculated with a single image using trigonometry as discussed above. Input from the GPS unit 206 may be used to determine current velocity of the vehicle 108. The driver's education evaluation system 100 may analyze the log of vehicle position relative to other vehicles to detect when time to collision decreases below a threshold value (e.g., 2 second etc.), which may indicate, for example, that the student driver 106 is tailgating the vehicle ahead (block 520). When a below threshold time to collision is detected, the client application 232 may make a time to collision below threshold log with a timestamp and/or location stamp (block 522). Alternatively or additionally, the data used to calculate time to collision may also be used to calculate similar metrics such as time to brake (i.e., the amount of time the student driver 106 has to apply the brakes in order to prevent collision with an object) and/or time to react (i.e., the amount of time a student driver 106 has to recognize an imminent collision and react to prevent it by swerving and/or applying the brakes). In addition to the data used to calculate time to collision, it may be advantageous to incorporate additional data into the calculation of time to brake and time to react such as the stopping capability of the vehicle 108, road conditions (e.g., wet, icy, unpaved, etc.), and the reaction time of the student driver 106 (e.g., determined by a test performed on the individual student driver 106, calculated by adjusting average human reaction time to account for the student driver's 106 age, health, performance level as determined herein, etc.). As with time to collision, time to brake and/or time to react may be compared to a threshold time and used to generate a performance log.

With the accelerometer logs, vehicle braking or deceleration may be monitored by noting deceleration sensed by an accelerometer oriented in the fore-aft direction of the vehicle (i.e., the X-axis) (block 526). If the force measured by the accelerometer array 224 indicates that the brakes of the vehicle 108 have been applied sharply (e.g., the force measured in the X-axis exceeds a threshold value) (block 528), the client application 232 may make a hard brake log with a timestamp and/or location stamp (block 530).

With the accelerometer logs, vehicle acceleration may be monitored by noting acceleration sensed by an accelerometer oriented in the fore-aft direction of the vehicle (i.e., the X-axis) (block 532). If the force measured by the accelerometer array 224 indicates that the accelerator of the vehicle 108 has been applied sharply (e.g., the force measured in the X-axis exceeds a threshold value) (block 534), the client application 232 may make a sharp acceleration log with a timestamp and/or location stamp (block 536).

With the accelerometer logs, vehicle lateral acceleration may be monitored by analyzing forces measured by an accelerometer oriented along the left to right side of the vehicle 108 (i.e., the Y-axis) (block 538). If the force measured by the accelerometer array 224 indicates that the vehicle 108 has swerved (e.g., the force measured in the Y-axis exceeds a threshold value) (block 540), the client application 232 may make a swerve log with a timestamp and/or location stamp (block 542).

In embodiments where the mobile device 110 and/or on-board computer 114 is a thin client device, the mobile device 110 and/or on-board computer 114 may send the logs to the server 140 soon after logging the recorded information. In such embodiments, the server 140 may analyze the logs of primary performance indicators as discussed above to determine secondary performance indicators.

Referring again to FIG. 3, after gathering primary and secondary performance indicators, the driver's education evaluation system 100 may analyze the primary and secondary performance indicators to generate one or more reports about the driving session (block 308).

Figure 6:
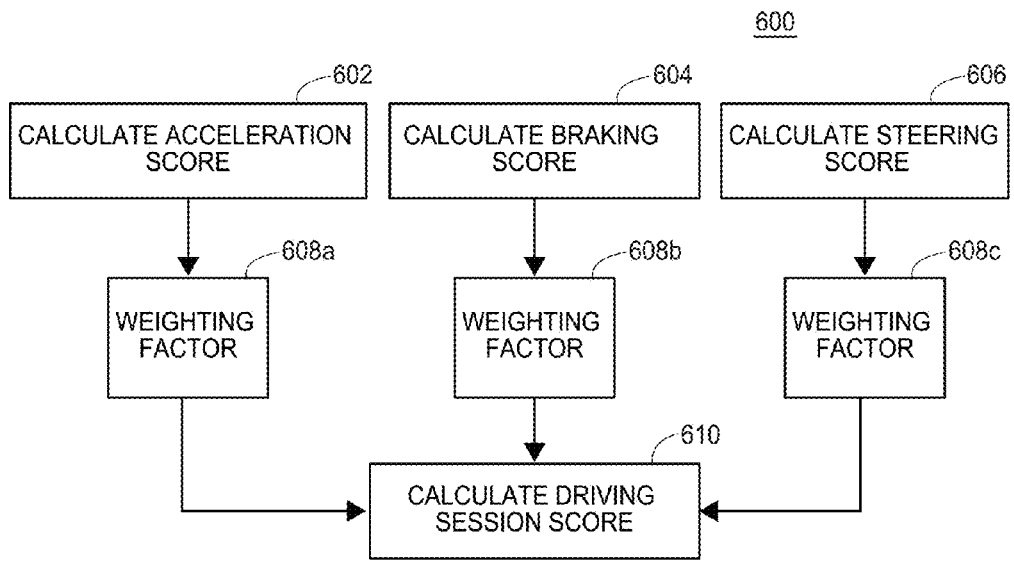
FIG. 6 depicts an exemplary embodiment of a driver's education evaluation score determination method for implementing the driver's education evaluation system in accordance with the presently described embodiments.
Figure 7:
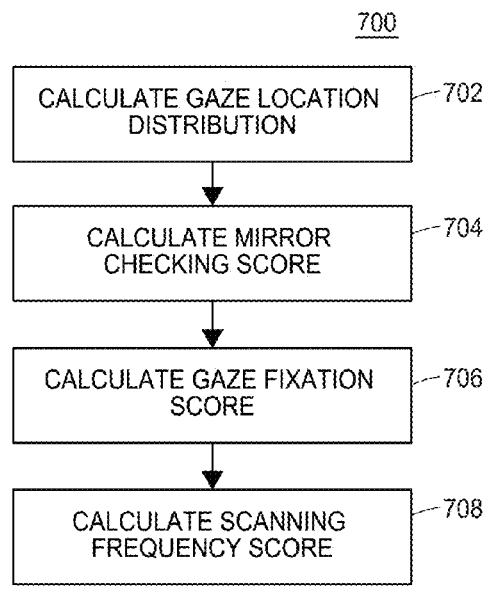
FIG. 7 depicts an exemplary embodiment of a driver's education evaluation scanning score determination method for implementing the driver's education evaluation system in accordance with the presently described embodiments.

Generating the one or more reports may include generating individual skill performance score(s) for the driving session for one or more gaze location score, a scanning frequency score, a gaze location score, a lane deviation score, a lane centering score, a time to collision score, a braking score, an acceleration score, or a steering score. Additionally or alternatively, the report may include one or more composite score(s) calculated using the individual skill performance score(s) that were generated. FIGS. 6 and 7 describe examples of how various individual skill performance scores and composite scores may be generated in exemplary embodiments. Further, the report(s) generated may include a recitation of important events that occurred during the driving session such as braking, acceleration, and/or swerving with forces exceeding a safety threshold (e.g., a hard brake at the intersection of Clark St. and Division St., a hard right turn at the intersections of LaSalle St. and Ohio St., etc.) with a timestamp and/or location stamp. The report may also include any comments made by the driving instructor during and after the driving session. It may be advantageous to represent these important events and comments visually on a map. After the report(s) have been generated, the report(s) may be distributed and/or displayed (block 310). The report(s) may be distributed via email or other type of electronic messaging to the driving instructor, the student driver, and/or the parents of the student driver. The report(s) may also be displayed on the display 202 of the mobile device 110 and/or on-board computer 114 or any other computing device being used by one or more of the student driver, parents, and driving instructor. Additionally, it may be advantageous to prepare a printed version of the report(s) and/or generate automated voicemail messages, and using known techniques. The generation and display of the report(s) is discussed in more detail below with respect to the example screenshots FIGS. 11-14. Such analysis, display, and distribution may be performed using the mobile device 110 and/or on-board computer 114, the server 140, or a combination.

FIG. 6 is a flow diagram depicting an exemplary embodiment of a driver's education evaluation score determination method 600 implemented by the driver's education evaluation system 100 while generating one or more reports about the driving session at block 308. The method 600 first determines an acceleration score using one or more performance logs (block 602). Acceleration score may be determined by subtracting points from a total score of 100 every time the student driver 106 applies too much acceleration during the driving session. The number of points subtracted may be determined according to a series of threshold values. For example, 1 point may be subtracted for a "hard" acceleration (e.g., acceleration above threshold A1 $m/s^2$), 2 points may be subtracted for a "very hard" acceleration (e.g., acceleration above threshold A2 $m/s^2$), and 3 points may be subtracted for a "severe" acceleration (e.g., acceleration above threshold A3 $m/s^2$). The method 600 may also determine a braking score using one of more performance logs (block 604). Braking score may be determined by subtracting points from a total score of 100 every time the student driver 106 applies too much braking (or deceleration) during the driving session. The number of points subtracted may be determined according to a series of threshold values. For example, 1 point may be subtracted for a "hard" braking (e.g., braking above threshold B1 $m/s^2$), 2 points may be subtracted for a "very hard" braking (e.g., braking above threshold B2 $m/s^2$), and 3 points may be subtracted for a "severe" braking (e.g., braking above threshold B3 $m/s^2$). The method 600 may also determine a steering score using one or more performance logs (block 606). The number of points subtracted may be determined according to a series of threshold values. For example, 1 point may be subtracted for a "hard" turning (e.g., turning above threshold T1 $m/s^2$), 2 points may be subtracted for a "very hard" turning (e.g., turning above threshold T2 $m/s^2$), and 3 points may be subtracted for a "severe" turning (e.g., turning above threshold T3 $m/s^2$). Of course, it will be understood that for each score different numbers of points may be subtracted and different units may be used. Further, it will also be understood that the scores may be calculated using methods other than subtraction from 100 such as adding points to a store for every acceleration, brake, and/or turn that does exceed the thresholds discussed above.

After determining scores for acceleration, braking, and steering as discussed above, the method 600 may multiply each score by a weighting factor 608a, b, c. For example, if each score is weighted equally, the weighting factors 610a-c may all be 0.333. However, it may be advantageous to weight one score higher than another. For example, sharp acceleration may be less important than braking and steering in evaluating the performance of the student driver 106. In such an embodiment, the weighting factors 610a-c may be 0.25, 0.35, and 0.40, respectively. In some embodiments, the weighting factors may be adjusted based on previous data for the user or for a large group of users. The weighting factors may be adjusted by one of the many known learning algorithms such as a support vector machine (SVM). The method 600 may then sum the weighted scores to determine a composite driving session score (block 610). The composite driving session score may be logged in with a timestamp and stored in data storage 228 and/or sent to the server 140 for remote storage. Alternatively, it will be understood that instead of a weighted sum adding up to a composite driving session score, the client application 232 may instead be a weighted sum that is subtracted from a maximum composite driving session score. An example of a display with the individual skill scores and composite driving session score may be seen in FIG. 12.

While the exemplary embodiment discussed above uses a 100 point scale, it will be appreciated that a 100 point scale is just one of many point scales that could be used (e.g., 50 point scale, 200 point scale, 500 point scale, 1000 point scale, etc.). Additional primary and secondary performance indicators may be used in the determination of the composite driving session score. For example, a gaze location score, a scanning frequency score, a gaze location score, a lane deviation score, a lane centering score, or a time to collision score may be added to the calculation of the composite driving session score. Each primary and secondary performance indicator may be used to generate a respective score similar to the scores described in connection to FIG. 6. For example, a respective score for each may be calculated by subtracting 1 point from a total score of 100 for every instance of a gaze fixation, slow lane deviation, failure to maintain lane centering, below threshold time to collision, respectively. Once a score for some or all of the gaze fixation, slow lane deviation, failure to maintain lane centering, below threshold time to collision performance has been calculated, scores may be added to the weighted sum discussed above. It will be appreciated that when additional scores are added to the weighted sum, it may be advantageous to change the weighting coefficient for some or all of the other scores in the weighted sum. Additionally, the driver's education evaluation system 100 may be configurable to adjust sensitivity, change point deduction values, etc.

FIG. 7 is a flow diagram depicting an exemplary embodiment of a driver's education evaluation scanning score determination method 700 implemented by the driver's education evaluation system 100 while generating one or more reports about the driving session at block 308. The method 700 may determine a gaze location distribution using the gaze locations logs (block 702). Because each gaze location log may include geographic coordinates corresponding to where the student driver 106 was looking at a particular time during the driving session, it may be advantageous to group the gaze location logs according to their coordinates. For example, it is likely that many gaze location logs were made when the student driver 106 was looking at one of the mirrors or the road ahead. Thus, even without knowledge of the interior layout of the vehicle 108, the method 700 may be able to determine where important features of the vehicle 108 are located based on the statistical distribution of gazes. A significant number of gazes to the far right may correspond to the right side mirror, a significant number of gazes to the upper center may correspond to the rear view mirror, etc. Accordingly, the method 700 may sort the gaze location logs into groups for right side mirror gazes, left side mirror gazes, rear mirror gazes, road gazes, and other gazes. The method 700 may be able to total the amount of time the student driver 106 was looking at each location and determine an average amount of time the eyes of the student driver 106 were not focused on the road ahead.

Using the gaze location distribution, the method 700 may calculate a mirror checking score (block 704). The mirror checking score may be determined by comparing the amount of time during the driving session that the student driver 106 spent gazing at the right side mirror, left side mirror, and rear view mirror to an expected amount of time. The expected amount of time may be a threshold level established by, for example, observing good drivers to determine how often each of the good drivers gaze at each mirror over a period of time (e.g., looking at each mirror for 0.5 second every 30 seconds). The mirror checking score may be calculated by subtracting points from 100 every time the student driver 106 fails to look at each mirror periodically at the expected amount during the driving session. Alternatively, using a dataset of driving performances by a large number of student drivers (e.g., other student drivers that have used the systems and methods described herein in the past), the driver's education evaluation system 100 may calculate a distribution of mirror checking performance. Using this distribution, the method 700 may calculate in which percentile the performance of the student driver 106 belongs, and store that percentile as the mirror checking score.

The method 700 may also determine a gaze fixation score using one or more performance logs (block 706). The gaze fixation score may be determined by subtracting 1 point from a total score of 100 every time gaze fixation is detected during a certain period of time. As with the mirror checking score discussed above, using a dataset of driving performances by a large number of student drivers (e.g., other student drivers that have used the systems and methods described herein in the past), the driver's education evaluation system 100 may calculate a distribution of gaze fixation performance. Using this distribution, the method 700 may calculate in which percentile the performance of the student driver 106 belongs, and store that percentile as the gaze fixation score.

The method 700 may also determine a scanning frequency score using one or more performance logs (block 708). Scanning frequency score can be determined by subtracting 1 point from a total score of 100 every time the student driver 106 fails to shift his or her gaze from one important area for vehicle operation (e.g., the road, mirrors, etc.) to another important area for vehicle operation within a threshold period of time (e.g., 5 seconds) within a certain period of time. For example, a student driver 106 who is distracted may not look from the road to check the mirrors and speed indicator with sufficient frequency. As with the mirror checking score discussed above, using a dataset of driving performances by a large number of student drivers (e.g., other student drivers that have used the systems and methods described herein in the past), the driver's education evaluation system 100 may calculate a distribution of scanning frequency performance. Using this distribution, the method 700 may calculate in which percentile the performance of the student driver 106 belongs, and store that percentile as the scanning frequency score. Each score may be logged in with a timestamp and stored in data storage 228 and/or sent to the server 140 for remote storage.

Figure 8:
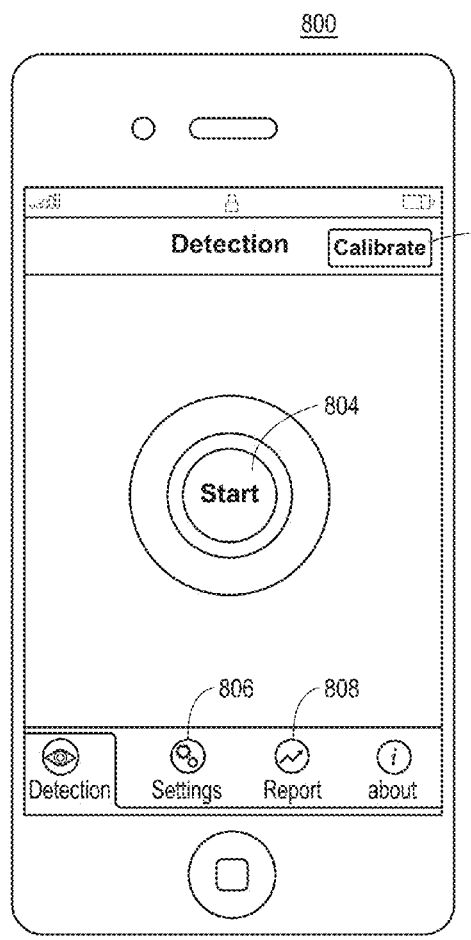
FIG. 8-10 are exemplary client applications pages to be displayed on a screen of a mobile device as part of the user interface used to implement the driver's education evaluation system in accordance with the presently described embodiments.
Figure 9:
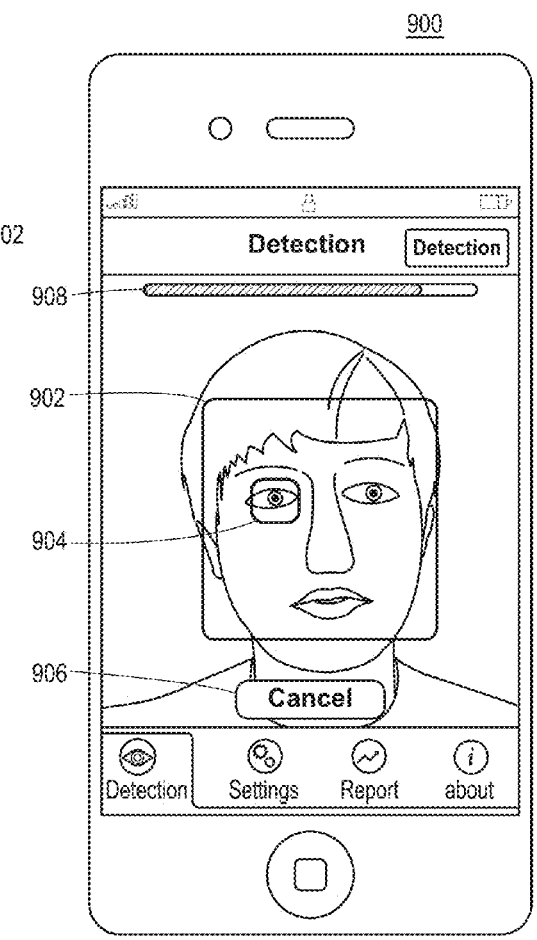
Figure 10:
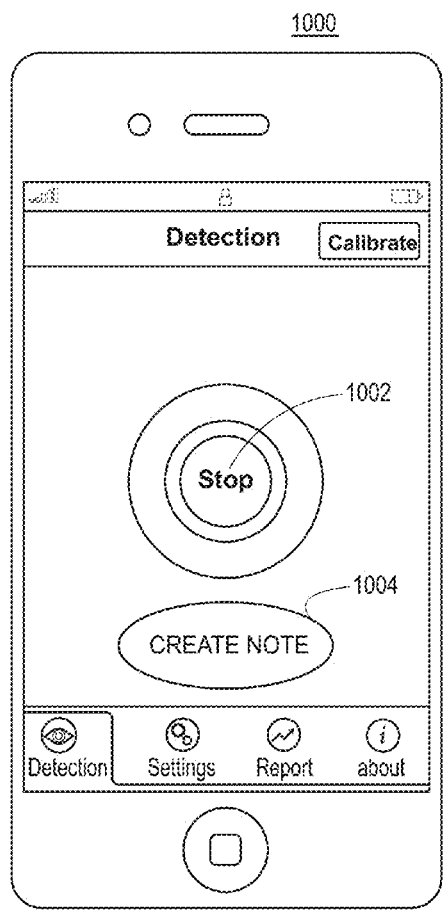

FIGS. 8-10 depict client application pages or screens that may be displayed on the display 202 of the mobile device 110 as part of the user interface used to implement the driver's education evaluation system 100. While FIGS. 8-10 depict client application pages or screens being displayed on the display 202 of the mobile device 110, it will be understood that the client application pages or screens could be displayed on the display 202 of the on-board computer 114 in addition to being displayed on the mobile device 110 or as an alternative. The client applications or pages may be generated by the mobile device 110 or sent to the mobile device 110 by the server 140 (e.g., as with a thin client). The user may launch the client application 232 from the mobile device 110 via any suitable manner, such as touch-selecting a client application icon (not shown) on the display 202 of the mobile device 110 or speaking a voice command into the microphone (not shown) of the mobile device 110. After the user launches the client application 232, the client application 232 may begin to run on the mobile device 110 as described above in connection to block 302.

With reference now to FIG. 8, a home screen 800 of the client application 232 may be displayed on the display 202 of the mobile device 110. The home screen 800 may include a "Calibrate" button 802, a "Start" button 804, a "Settings" tab 806, and a "Report" tab 808. When the user selects the calibrate button 802 the client application 232 may execute a calibration routine as described above in connection to block 304.

With reference now to FIG. 9, a calibration screen 900 of the client application 232 may be displayed on the display 202 of the mobile device 110 during a calibration routine executed in connection to block 304. The calibration screen 900 may include a face detection indicator 902, eye detection indicator 904, the "Cancel" button 906, and a calibration progress indicator 908. While the client application 232 is executing the calibration routine discussed in connection to block 304, the calibration screen 900 may display a face detection indicator 902 showing on the display 202 the visual area perceived by the client application 232 to be the face of the user 106 and/or an eye detection indicator 904 showing on the display the visual area perceived by the client application 232 to be an eye of the user 106. If a user selects the cancel button 906, calibration may be terminated. A calibration progress indicator 908 may display an approximate indication of the status of the calibration routine.

Referring again to FIG. 8 when the user selects the "Start" button 804, the client application 232 may begin to collect data during the driving session in connection to block 306. With reference now to FIG. 10, driving session data collection screen 1000 may be displayed on the display 202 of the mobile device 110 executed in connection with block 306. The driving session data collection screen 1000 may include a "Stop" button 1002. If the "Stop" button 1002 is selected by the user, the vehicle operator impairment monitoring system 100 may terminate operator impairment monitoring. Selecting the "Stop" button 1002 may also permit the user to save additional information about the trip such as additional instructor comments. The driving session data collection screen 1000 may also include a "Create Note" button 1004. If the driving instructor activates the "Create Note" button, the instructor may be able to enter a textual and/or audible comment pertaining to the driving session as discussed in connection to block 412.

Figure 11:
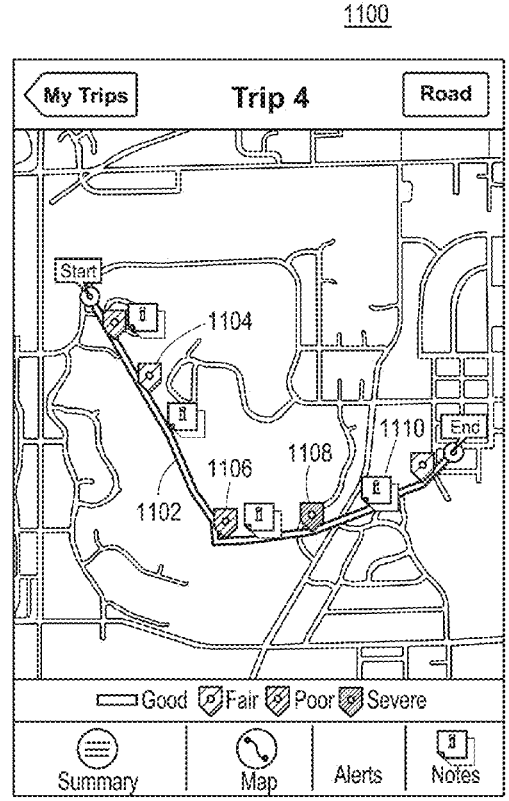
FIG. 11-15 are exemplary reports generated by the driver's education evaluation system in accordance with the presently described embodiments.

Now referring to FIG. 11, another example screenshot 1100 illustrates a report map including driving session data. The screenshot 1100 may be generated using the techniques discussed in connection to block 308 and displayed using the techniques discussed in connection to block 310. The map includes a visual representation of the route 1102 taken by the student driver 106 during the driving session. At various points on the route may be projected icons indicating the occurrence of important events that occurred during the driving session such as those detected in connection to block 306 (e.g., hard braking events, sharp turns, etc.). These icons may be used to indicate good driving (e.g., drawing the route 1102 in green) and instances of less than good driving by degree. For example, a yellow flag 1104 may indicate "fair" driving (e.g., a "hard" brake as discussed above), an orange flag 1106 may indicated "poor" driving (e.g., a "very hard" brake as discussed above), and a red flag 1108 (e.g., a "severe" brake as discussed above). Additionally, location-based comments may be indicated with a comment flag 1110. The route 1102 and various icons 1104-1110 may be projected onto a map in the appropriate place using the location stamps included with the performance logs as discussed above.

Figures 12, 13:
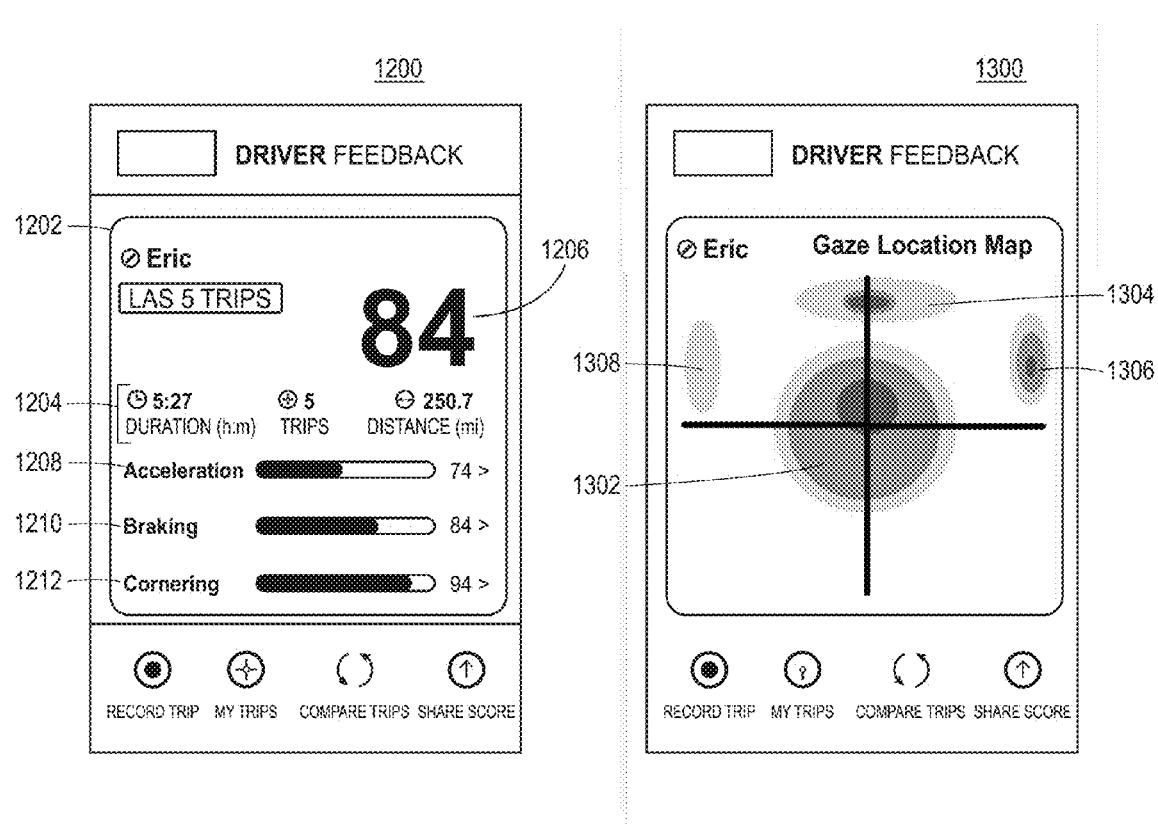

Now referring to FIG. 12, another example screenshot 1200 illustrates a numerical report for a driving session. The screenshot 1200 may be generated using the techniques discussed in connection to block 308 and displayed using the techniques discussed in connection to block 310. In particular, the screenshot 1200 may be generated using the techniques discussed in connection to FIG. 6. The numerical report may be generated based on a single driving session or multiple driving sessions as shown in FIG. 12. The numerical report may include information about the student driver 1202 (e.g., name, an indicator of how many driving sessions are included in the numerical report, a photograph, etc.) and information about the driving session 1204 (e.g., total duration of driving sessions, the number of trips included in the numerical report, and a total distance of driving sessions). The numerical report may include a composite score 1206, an acceleration skill score 1208, a braking skill score 1210, and/or a cornering skill score 1212. Additionally, it may be advantageous to display additional skill scores and indicators such as a lane maintenance score or time to collision score discussed above.

Now referring to FIG. 13, another example screenshot 1300 illustrates a visual mapping of gaze location distribution from a driving session. The screenshot 1300 may be generated using the techniques discussed in connection to block 308 and displayed using the techniques discussed in connection to block 310. In particular, the screenshot 1300 may be generated using the techniques discussed in connection to block 702 of FIG. 7. The visual mapping of gaze location distribution may be drawn as a "heat map" showing the density of the statistical distribution of gaze locations using a progressive color palette. For example, white may indicate little to no density, yellow may indicate low density, orange may indicate medium density, and red may indicate high density (i.e., where the student driver 106 was looking most often). The visual mapping of gaze location distribution may include distributions associated with the student driver looking at the road 1302, looking at the rear view mirror 1304, looking at the left side mirror 1306, and/or looking at the right side mirror 1308. The visual mapping of gaze location distribution may indicate suggestions for how the student driver 106 may include performance. For example, in the screenshot 1300, the distribution 1308 does not show any orange or red, indicating that the student driver 106 may not be checking the right side mirror enough. Accordingly, the driving instructor may advise the student driver 106 to check the right side mirror during the next driving session.

Figure 14:
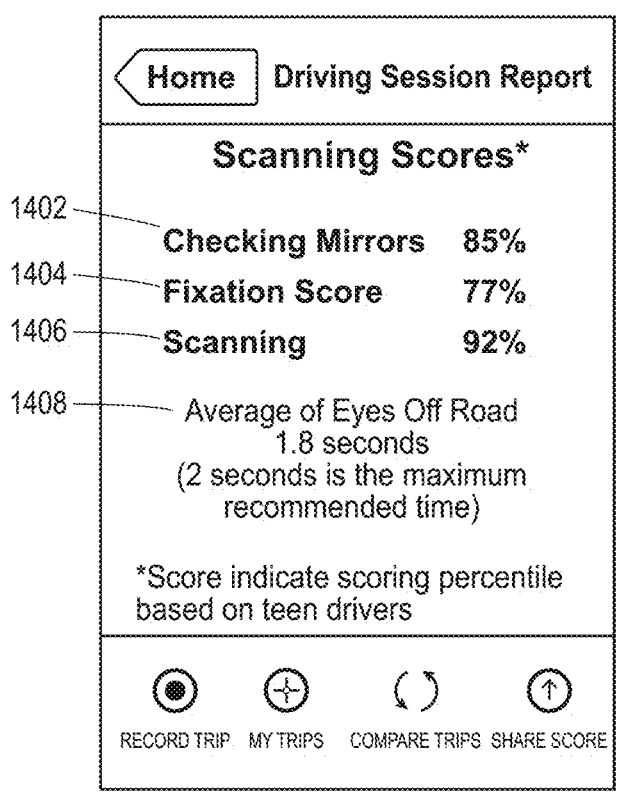

Now referring to FIG. 14, another example screenshot 1400 illustrates a scanning score report from a driving session. The screenshot 1400 may be generated using the techniques discussed in connection to block 308 and displayed using the techniques discussed in connection to block 310. In particular, the screenshot 1400 may be generated using the techniques discussed in connection to FIG. 7. The scanning score report may include a score 1402 for checking mirrors, a gaze fixation score 1404, a scanning score 1406 (e.g., a scanning frequency score), and/or an indication 1408 of the average amount of time the student driver 106 spent with his or her eyes off the road.

Using the systems and methods discussed above, a driving instructor may take one or more student drivers 106 on one or more driving sessions. Data may be gathered during each driving session and reports may be generated for each driving session as discussed above. The driving instructor may take the same student driver 106 out for multiple driving sessions over the course of a driving class (e.g., one driving session per weekly class). The data and reports associated with each driving session may be used to evaluate the progress of the student driver over the course of the driving class, in particular to determine whether the skills of the student driver are improving. The data and reports associated with each driving session may also be used to advise the student driver on which skills he or she needs to practice between driving classes. Further, the driving instructor may use the systems and methods discussed above to evaluate a plurality of students in the driving class. The data and reports associated with each driving session may be used to evaluate the students in the class relative to each other for the purposes of assigning grades (e.g., an "A" for students in the top quartile of the class, a "B" for the students in the middle two quartiles, etc.) and generating reports on the driving performance for the class. Further, the driving school employing the driving instructor may use the data and reports to evaluate the skills of the driving instructor or the driving school itself. For example, it may be advantageous to determine whether the classes taught by a particular instructor demonstrate improved skills over the course of the class. It may also be advantageous for the driving school to determine whether the classes taught at the driving school are effective at improving driving skills to improve curricula, apply for grants, etc.

Figure 15:
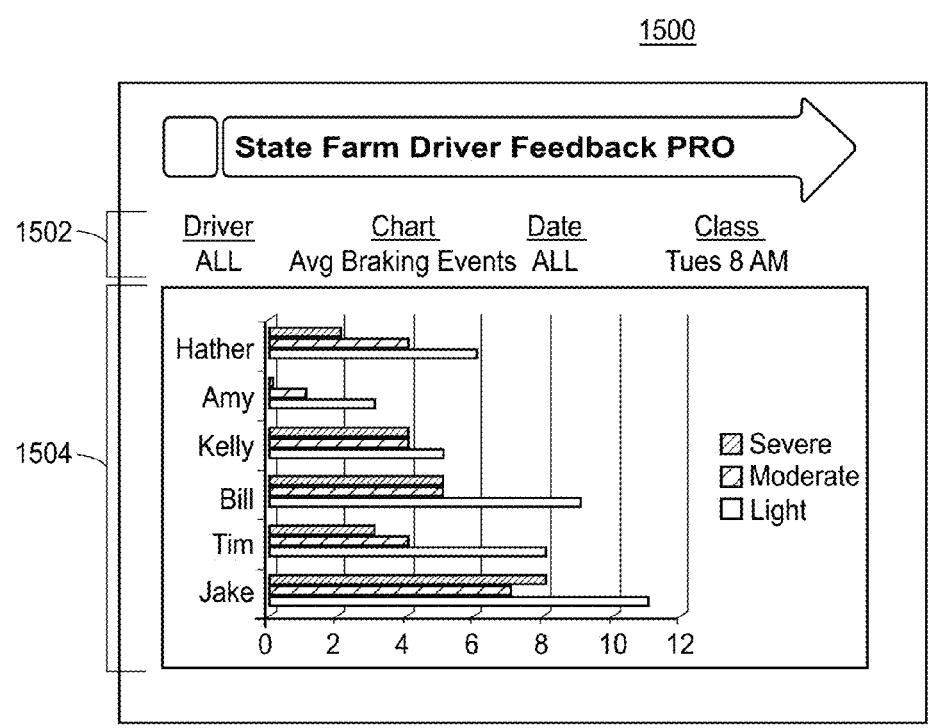

Now referring to FIG. 15, another example screenshot 1500 illustrates a driver's education class report from a series of driving sessions. The screenshot 1500 may be generated using the techniques discussed in connection to block 308 and displayed using the techniques discussed in connection to block 310. In particular, screenshot 1500 shows a numerical tally of the light, moderate, and severe braking events recorded during the driving sessions associated with a particular class (i.e., Tuesday at 8 AM). The screenshot 1500 may list information 1502 about the class and a visualization 1504 of the braking event tallies. The visualization allows the instructor and driving school to make a quick evaluation of the performance of each student driver in the class. For example, it is clear from the graph that "Jake" has many more braking events than "Amy." Of course, it will be appreciated that any primary or secondary indicators or the scores derived therewith may be represented in a similar manner. For example, a second screenshot 1500 (not shown) may display the average speed of each student driver in the class. If, for example, the second screenshot 1500 (not shown) shows that "Amy" drove at a very low speed during the driving session, then a more complete comparison of the driving sessions may be made (e.g., Amy did not apply the brake sharply because she was already driving too slow). Thus, while Amy performed the best in the class at braking, she may lose points on her grade because of her slow speed relative to the other members of the class.

Of course, it will be understood that the reports displayed on the screenshots 1100, 1200, 1300, 1400, and 1500 may displayed in ways other than being displayed on the screen 202. For example, the reports may be printed on paper. The reports may also be distributed as discussed above using any suitable technique.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed:

1. A method comprising:
    for each of two or more driving sessions in which a student driver operates a vehicle:
        gathering, from one or more sensors in a mobile device, driving skill data indicative of at least one of behavior of the student driver, acceleration of the vehicle, braking of the vehicle, or steering of the vehicle, wherein the one or more sensors in the mobile device include at least one of the following: an accelerometer array or a geopositioning device, and
        generating a driving session report corresponding to the respective one of the two or more driving sessions by an application specifically configuring a computing device to generate the driving session report, wherein generating the driving session report includes calculating, for the respective one of the two or more driving sessions, at least one score based on the driving skill data, and wherein a weighting factor of the application is specifically adjusted for the student driver;
    causing, by the application specially configuring the computing device, the driving session reports corresponding to the two or more driving sessions to be displayed to a driving instructor on a display device;
    in response to displaying the driving session reports corresponding to the two or more driving sessions, receiving comments from the driving instructor about the two or more driving sessions of the student driver; and
    storing, by the application on a non-transitory computer-readable medium, the driving session reports corresponding to the two or more driving sessions along with the received comments from the driving instructor.

2. The method of claim 1, further comprising causing, by the application specially configuring the computing device, the driving session reports corresponding to the two or more driving sessions along with the received comments from the driving instructor to be displayed to the student driver.

3. The method of claim 1, wherein gathering the driving skill data includes gathering a plurality of gaze location logs, each of the plurality of gaze location logs indicating a duration of a gaze of the student driver in a particular direction.

4. The method of claim 1, wherein gathering the driving skill data includes gathering acceleration data from an array of accelerometers.

5. The method of claim 1, wherein generating the driving session report corresponding to the respective one of the two or more driving sessions including calculating the at least one score includes:
    calculating a plurality of scores, each of the plurality of scores corresponding to a respective one of gaze location, scanning frequency, lane deviation, lane centering, time to collision, braking, acceleration, or steering of the student driver during the two or more driving sessions, and
    combining the plurality of scores to generate a composite score representative of a performance of the student driver during the respective one of the two or more driving sessions,
    wherein the driving session report includes at least one of the plurality of scores and the composite score.

6. The method of claim 1, further comprising, for each of two or more driving sessions, detecting, by the application specially configuring the computing device, one or more events occurring during the respective one of the two or more driving sessions based on the gathered driving skill data.

7. The method of claim 6, wherein generating the driving session report corresponding to the respective one of the two or more driving sessions includes generating indications of the one or more events occurring during the respective one of the two or more driving sessions, wherein the driving session report includes the indications of the one or more events.

8. A system comprising:
    a user interface;
    one or more sensors configured to generate driving skill data indicative of at least one of behavior of a student driver, acceleration of a vehicle, braking of the vehicle, or steering of the vehicle, including at least one of the following: an accelerometer array or a geopositioning device;
    a non-transitory memory storing computer-readable instructions; and
    one or more processors specially configured by the computer-readable instructions such that, when executed by the one or more processors, the computer-readable instructions cause the one or more processors to:
        for each of two or more driving sessions in which the student driver operates the vehicle:
            gather, from the one or more sensors, the driving skill data indicative of the at least one of behavior of the student driver, acceleration of the vehicle, braking of the vehicle, or steering of the vehicle, and
            generate a driving session report corresponding to the respective one of the two or more driving sessions including calculating, for the respective one of the two or more driving sessions, at least one score based on the driving skill data and based on a weighting factor, wherein the weighting factor is specifically adjusted for the student driver,
        cause the driving session reports corresponding to the two or more driving sessions to be displayed on the user interface;
        in response to displaying the driving session reports corresponding to the two or more driving sessions, receive, via the user interface, comments about the two or more driving sessions of the student driver; and
        store the driving session reports corresponding to the two or more driving sessions along with the received comments.

9. The system of claim 8, wherein the one or more sensors include an accelerometer.

10. The system of claim 8, wherein the one or more sensors include a camera.

11. The system of claim 8, wherein the one or more sensors include an accelerometer and a camera.

12. The system of claim 11, wherein the at least one score includes an acceleration, braking, or steering score based on first portions of the driving skill data generated by the accelerometer and a gaze location, scanning frequency, lane deviation, lane centering, or time to collision score based on second portions of the driving skill data generated by the camera.

13. The system of claim 8, wherein the one or more sensors include a front image capture device and a back image capture device, wherein the front image capture device in configured to capture images of the student driver, and wherein the back image capture device is configured to capture images of the environment surrounding the vehicle.

14. The system of claim 8, wherein the one or more sensors includes an accelerometer, wherein the at least one score includes an acceleration, braking, or steering score, and wherein generating a driving session report corresponding to the respective one of the two or more driving sessions including calculating the at least one score includes:
- based on the driving skill data generated by the accelerometer, detecting one or more times during the respective one of the two or more driving sessions at which an acceleration indicated in the driving skill data is above or below a threshold, and
- for each of the detected one or more times, modifying a pre-defined number to generate the acceleration, braking, or steering score.

15. The system of claim 8, wherein the one or more sensors includes a camera, wherein the at least one score includes a gaze location, scanning frequency, lane deviation, lane centering, or time to collision score, and wherein generating a driving session report corresponding to the respective one of the two or more driving sessions including calculating the at least one score includes:
- based on the driving skill data generated by the camera, detecting one or more instances during the respective one of the two or more driving sessions of a gaze fixation, a lane deviation, a failure to maintain lane centering, or a time to collision below a threshold, and
- for each of the detected instances, modifying a pre-defined number to generate the gaze location, scanning frequency, lane deviation, lane centering, or time to collision score.

16. A non-transitory computer-readable medium storing instructions that specially configure a computer system such that, when executed by one or more processors of the computer system, the instructions cause the computer system to:
- for each of two or more driving sessions in which a student driver operates a vehicle:
  - gather, from one or more sensors, driving skill data indicative of at least one of behavior of the student driver, acceleration of the vehicle, braking of the vehicle, or steering of the vehicle, wherein the one or more sensors in the mobile device include at least one of the following: an accelerometer array or a geopositioning device, and
  - generate a driving session report corresponding to the respective one of the two or more driving sessions including calculating, for the respective one of the two or more driving sessions, at least one score based on the driving skill data and based on a weighting factor, wherein the weighting factor is specifically adjusted for the student driver;
- cause the driving session reports corresponding to the two or more driving sessions to be displayed to a driving instructor on a display device;
- in response to displaying the driving session reports corresponding to the two or more driving sessions, receive comments from the driving instructor about the two or more driving sessions of the student driver; and
- store the driving session reports corresponding to the two or more driving sessions along with the received comments from the driving instructor.

17. The non-transitory computer-readable medium of claim 16, wherein calculating the at least one score includes:
- based on the driving skill data, detecting one or more events occurring during the respective one of the two or more driving sessions, and
- for each of the one or more events, deducting a point value from a pre-defined number to generate the at least one score.

18. The non-transitory computer-readable medium of claim 17, wherein the instruction further cause the computer system to receive, via a user interface, a deduction configuration, wherein the deduction configuration defines the point value utilized in the calculating of the at least one score.

19. The non-transitory computer-readable medium of claim 17, wherein the instruction further cause the computer system to receive, via a user interface, the weighting factor, wherein the weighting factor defines, for the student driver, variations in the driving skill data that are indicative of the one or more events.

20. The non-transitory computer-readable medium of claim 16, wherein calculating the at least one score includes:
- based on a dataset indicative of previous driving performances of a plurality of reference drivers different than the student driver, determining a distribution indicative of driving performance,
- based on the driving skill data, determining a current driving performance of the student driver, and
- determining, as the at least one score, a percentile corresponding to the student driver based on the current driving performance and the distribution indicative of driving performance.

* * * * *